United States Patent [19]
Cohen

[11] Patent Number: 5,336,252
[45] Date of Patent: Aug. 9, 1994

[54] SYSTEM AND METHOD FOR IMPLANTING CARDIAC ELECTRICAL LEADS

[76] Inventor: Donald M. Cohen, 17512 Luther Ave., Irvine, Calif. 92714

[21] Appl. No.: 901,991

[22] Filed: Jun. 22, 1992

[51] Int. Cl.$^5$ ............................................. A61N 1/39
[52] U.S. Cl. .................................. 607/119; 607/116; 607/126
[58] Field of Search ............... 607/116, 119, 122, 123, 607/125, 126, 129, 130, 131; 128/642, 643, 644

[56] References Cited

U.S. PATENT DOCUMENTS

| | | | |
|---|---|---|---|
| 4,166,469 | 9/1979 | Littleford | 607/122 |
| 4,774,952 | 10/1988 | Smits | 128/419 |
| 4,787,389 | 11/1988 | Tarjan | 128/419 |
| 4,817,634 | 4/1989 | Holleman et al. | 128/784 |
| 4,865,037 | 9/1989 | Chin et al. | 128/419 |
| 4,884,567 | 12/1989 | Elliott et al. | 128/303 |
| 4,946,457 | 8/1990 | Elliott | 606/1 |
| 4,991,578 | 2/1991 | Cohen | 128/419 |
| 4,991,603 | 2/1991 | Cohen et al. | 128/786 |
| 4,998,975 | 3/1991 | Cohen et al. | 128/419 |

OTHER PUBLICATIONS

Hauser, et al., "Current Status of the Ventak ® PRx Pulse Generator and Endotak ™ Nonthoracotomy Lead System", *PACE* vol. 15, pp. 671677 (Apr. 1992).
Block, et al., "Results and Realistic Expectations with Transveneous Lead Systems", *PACE*, vol. 15, 665-670 (Apr. 1992).
Akhtar, et al., "Role of Implantable Cardioverter Defibrillator Therapy in the Management of High-Risk Patients", *Supplement I Circulation*, vol. 85:1, pp. 1-13-1-1-139 (Jan. 1992).
Jones, et al., "Biphasic Versus Sequential Pulse Defibrillation: A Direct Comparison in Pigs", *American Heart Journal*, pp. 97-103 (Jul. 1992).
McCowan, et al., "Automatic Implantable Cardioverter-Defibrillator Implantation Without Thoracotomy Using Endocardial and Submuscular Path System", *JACC*, vol. 17:2, pp. 415-421 (Feb. 1991).

Primary Examiner—Lee S. Cohen
Assistant Examiner—Jeffrey R. Jastrzab
Attorney, Agent, or Firm—Fitch, Even, Tabin & Flannery

[57] ABSTRACT

The present invention provides a system and method for implanting electric leads in the pericardial space of a heart. The system includes a suction cup mounted to the distal end of a guiding catheter. A vacuum pump evacuates the guiding catheter whereby the suction cup is held against the pericardium. An endoscope fitted through the guiding catheter is used to observe the surface of the pericardium. A needle selectively deployable from the end of a flexible wire guide is fitted through the guiding catheter and cuts an access hole through the pericardium into the pericardial space. The distal tip of the wire guide is deflected into a "J" shape to anchor the wire guide in the pericardial space. A dilator having a blunt, tapered end and a longitudinal bore slides over the wire guide and is advanced to the pericardial space to dilate the access hole. A flexible sheath slides over the dilator to form a channel when the dilator is withdrawn from the wire guide. An electric lead is advanced through the channel to penetrate the pericardial space and is secured therein with an anchor flange at the end of the electrical lead.

6 Claims, 22 Drawing Sheets

SYSTEM AND METHOD FOR IMPLANTING CARDIAC ELECTRICAL LEADS

FIELD OF THE INVENTION

The present invention relates generally to cardiac defibrillation systems and more particularly to methods and equipment for implanting cardiac defibrillation leads in the pericardial space between the pericardium and myocardial tissue of a mammalian heart.

BACKGROUND OF THE INVENTION

A healthy, rhythmic heart beats regularly to pump blood throughout the body. When the heart is experiencing an arrhythmia it does not pump blood as effectively. The most severe of all arrhythmias is ventricular fibrillation (V-fib). V-fib is a condition in which the heart experiences circus movement; that is, it contracts in an unsynchronized, discordant manner. During V-fib, the heart virtually ceases to pump blood and death is imminent unless a normal heart beat is restored.

A defibrillator is a device that provides energy in the form of a large electrical pulse or pulses to the heart for the purpose of interrupting the circus rhythm. A successful defibrillation interrupts the fibrillation and restores a more normal, life sustaining rhythm. A defibrillator may be either external or implantable. A defibrillator has electrodes that are placed on or in the body which provide an interface through which defibrillation energy is delivered to the body.

Some patients have a particularly high susceptibility to V-fib. For such patients, it is desirable to implant a defibrillator that has the potential to continuously sense the rhythm of the heart and deliver the defibrillating energy whenever it is needed. Such continuous sensing obviates the need for a patient to be continually monitored by medical personnel.

Defibrillators that are implanted within the body are necessarily relatively small in order to fit within the restricted space available in a human body. This space restriction imposes limits on the amount of electrical energy that may be stored in the defibrillator that is available for generating defibrillation pulses. Such electrical energy is typically stored in batteries positioned within the defibrillator. So that the implantable defibrillator may operate a long time before its battery is depleted, it is desirable to minimize the energy expenditure required for each defibrillation pulse. One way of reducing the defibrillation energy storage requirements is to deliver the energy in a very efficient manner.

Efficient delivery of defibrillation pulses may be accomplished by placing the defibrillating electrodes close to the heart. This is commonly achieved (as in U.S. Pat. Nos. 3,942,536, 4,161,952 and 4,355,646) by conducting the energy from the defibrillator to the heart through flexible, insulated leads that are generally connected to electrodes that are placed on, or very near to the heart.

To further minimize the energy required to defibrillate the heart, prior art defibrillation systems have used a variety of electrode shapes, materials, locations and even electrical wave forms and pulse trains. The electrodes that generally permit defibrillation with the lowest electrical energy expenditure have typically been placed directly on or very close to the heart. Such electrodes are referred to as patch electrodes. These electrodes also have relatively large surface areas, so that they cover a good deal of the surface of the ventricles of the heart.

Since the electrical current associated with a defibrillation pulse is conducted out of one electrode and back into the other, the locations where the electrodes are placed on the heart have a significant influence on the energy expenditure needed for defibrillation. Efficient delivery of defibrillating energy is associated with a fairly uniform energy density (energy per volume area) distribution throughout the ventricles. Uniform energy density through the ventricles allows the entire ventricular mass to be simultaneously depolarized without expending excess energy. Excessive energy is not only inefficient, it also may actually cause irreversible damage to the heart, for example by burning heart tissue. The inefficient use of energy shortens the expected life of the implantable defibrillator, and may even result in defibrillation thresholds so high that the heart can not be defibrillated by the implanted defibrillator. A defibrillation threshold is the energy level required to effectuate defibrillation of the heart.

Accordingly, access to the heart is necessary to facilitate the most advantageous placement of the defibrillating electrodes in a manner which promotes uniform energy distribution through the ventricles and which minimizes the energy expenditure required to effectuate defibrillation. Typically, attachment of defibrillation electrodes to the heart requires an open chest procedure; either via a median sternotomy; intercostal approach; or, in a more limited procedure, a sub-xiphoid approach. All of these procedures involve major surgeries which are painful and dangerous for the patient.

Alternative methods of placing defibrillation electrodes are less invasive. Such less intrusive methods employ transvenously placed endocardial electrodes and/or subcutaneous electrodes. Transvenously placed endocardial electrodes are placed inside the heart by threading them through a large vein, such as the vena cava. Subcutaneous electrodes are placed under the skin somewhere in the upper thorax in locations relatively distant from the heart. Electrodes placed solely by these means generally result in much higher defibrillation thresholds than exhibited by patch electrodes sutured directly to the heart.

An automatic implantable defibrillation system continually monitors the heart rhythm for V-fib or other lethal arrhythmias. When the defibrillation system recognizes a lethal arrhythmia, where the heart fails to pump blood to the body, the defibrillator delivers one or more electrical energy pulses to the heart to re-establish a life sustaining rhythm. An automatic defibrillation system obviates the need for a patient to wait for the arrival of trained medical personnel to diagnose and treat a lethal arrhythmia.

An object of many defibrillation lead implant procedures is to not only place the leads effectively, but to do so with a minimum of trauma to the patient. Minimization of trauma should be associated with a concomitant reduction in morbidity and mortality for the patients undergoing such procedures. Rather than have a patient undergo an open chest procedure (thoracotomy), even a limited one, it is desirable to employ a procedure entailing less risk and discomfort for the patient. Therefore, there is a need for methods and equipment that enable the effective placement of defibrillation electrodes on or near the heart in a manner which minimizes trauma, risk, and discomfort for the patient.

The heart resides within a thin, lubricous, protective sac known as the pericardium which is a membranous sac that encloses the heart. It consists of an outer layer of dense fibrous tissue and an inner serous layer, termed the epicardium, which directly surrounds the heart. Throughout the description and claims herein, the phrase "within the pericardium" or "within the pericardial space" refers to any of the body tissues or fluid found inside the dense outer surface of the heart, but not including the interior of the heart. The narrow space between the pericardium and the heart is filled with a thin layer of pericardial fluid and is referred to as the pericardial space.

It is generally known that the pericardial space represents a propitious location for defibrillation electrode placement. For example, U.S. Pat. No. 4,991,578 describes a system for positioning a defibrillation electrode within the pericardial space of a mammal The system described in the '578 patent includes means for distending the pericardium from the heart by injecting a small volume of fluid into the pericardium, e.g., from a location inside the heart. A needle having a lumen therethrough is inserted from a sub-xiphoid or other percutaneous position into the body until a tip thereof punctures the distended pericardium at a selected location. A guidewire is inserted into the pericardium through the lumen of the needle, and while the guidewire remains in the pericardial space, the needle is removed. A sheath is introduced over the guidewire, with the aid of a dilator, and inserted into the tissue until the end of the sheath is positioned within the pericardium. The defibrillation lead, with its electrode in a retracted position, is inserted through the sheath until the electrode is likewise positioned within the pericardium, whereupon the electrode is deployed in order to make contact with a large area of tissue within the pericardium.

However, in some patients, access to the pericardial space is not readily achievable, due to the presence of proliferative adhesions between the pericardium and the heart. Application of the '578 system would not benefit such patients because injection of fluid between the pericardium and the heart would not result in distension of the pericardium. The system described in the '578 patent disadvantageously requires perforation of the heart wall. Such perforation can result in severe bleeding, requiring emergency open thoracic surgery.

Using only currently available techniques, pericardial access on defibrillation patients can be a dangerous proposition. The pericardium is both very thin and close to the heart. In most patients it is difficult to cut or puncture the pericardium without also inadvertently cutting or perforating the myocardium (the heart muscle) or a coronary vessel.

To place a sheath in a vessel by the technique known in the art as a percutaneous stick, a needle is placed into the desired vessel, a guidewire is placed through the needle, and then the needle is removed. Then a dilator/sheath passes over the guidewire and into the vessel. A similar technique could be adapted to gain access to the pericardium for the purpose of lead placement. There are at least two potential impediments to direct placement of a dilator/sheath introducer set into the pericardium: (1) relatively loose attachment of the pericardium with respect to the chest wall may make passage of a dilator through the very tough pericardium difficult; and (2) rapid, inadvertent introduction of the dilator into the pericardium could easily impale the myocardium or a coronary vessel. Thus, there is a need for equipment and methods to safely enter the pericardial space with an introducer sheath.

The site at which the surgical instruments are brought into the proximity of the heart is very important. All actions in this vicinity must be careful and deliberate. Because the heart is in constant motion, it is very difficult to avoid damaging the heart. There are no instruments known in the art that permit precisely metered motion relative to the moving surface of the heart. If a sharp instrument were to impinge upon a beating heart, an unintended perforation of a coronary artery or myocardial wall could occur. Such perforation would result in massive bleeding, endangering the life of the patient, and probably necessitating emergency open chest surgery.

There are no safe and effective percutaneous methods and instruments known in the art for placing defibrillation leads either in the pericardial space or extrapericardially (outside the pericardium) with anchoring close to the heart. There are no defibrillation leads known in the art that are ideally suited to being placed through percutaneous introducers and situated in the pericardium or on the pericardium with anchoring close to the heart. Therefore, there is great need for a method and system for implanting defibrillation leads to the surface of the heart or pericardium that provides good anchoring and that does not require perforation of the heart tissue and exposure of the patient to the risk of severe bleeding and possibly death.

SUMMARY OF THE INVENTION

The disadvantages and limitations of the background art discussed above are overcome by the present invention. With this invention, a method and system for positioning and anchoring defibrillation electrode(s) on or very close to the epicardium are disclosed. One of the most critical considerations of the method and system of the present invention lies in gaining direct percutaneous access to the pericardial space without puncturing or otherwise damaging the heart. This is because, in the absence of a pericardial effusion, any attempt to introduce a sharp object percutaneously with the intent of piercing the pericardium would almost certainly also invade the myocardium. The methods and system of the present invention allow implantation of defibrillation leads or anchoring devices into the pericardial space with small instruments employed through introducers that penetrate the chest wall. No substantial incisions are needed, only holes large enough for the lead introducer are required.

Bounded by the left and right pleural (lung) sacs in the region known as the mediastinum, lies the heart. There are several sites of attachment of the pericardium in this region, but over most of its surface it is free of attachments. There is a virtual space separating each of the pleural sacs from the pericardium. Under normal circumstances the pleural sacs are in very close proximity to the pericardium. The pericardial and pleural sacs slide past each other as the heart and lungs change volume at their respective rhythms. The lungs fill the space that is allotted to them, and, due to their extraordinary compliance, conform around the pericardium. Therefore, lung retraction is an important step in any percutaneous procedure for gaining access to the heart.

The present invention may be characterized as a system for implanting electric leads in or on the pericardium of a heart. Access to the mediastinum is gained using conventional instruments and techniques. The system includes a guiding catheter. The guiding catheter may be deployed from a percutaneous trocar loaded into the mediastinum. The guiding catheter has a channel for a miniscope, a channel for instrumentation and a channel for suction. At the distal tip of the guiding catheter is a suction cup. A vacuum pump evacuates the guiding catheter suction channel so as to attach the suction cup to the pericardium. An endoscope fitted through the guiding catheter permits observation of the surface of the pericardium. The surface of the heart may also be seen through the pericardium. A needle selectively deployable from the end of a flexible wire guide is fitted through the guiding catheter instrument channel and cuts an access hole through the pericardium into the pericardial space. The distal tip of the wire guide is inserted well into the pericardial space and deflected into a "J" shape to anchor the wire guide in the pericardial space. A dilator having a blunt, tapered end and a longitudinal bore slides over the wire guide and is advanced to the pericardial space to dilate the access hole. A flexible sheath slides over the dilator to form a channel when the dilator and guidewire are withdrawn. An electric lead is advanced through the sheath to penetrate the pericardial space and is secured there with anchors attached to the distal end of the lead.

The present invention may also be characterized as a method for implanting electrically conductive lead electrodes or their anchors in the pericardium of a mammalian heart. The method comprises the steps of: creating a first percutaneous access to the mediastinum of the mammal; creating a second percutaneous access to the mediastinum of the mammal; observing the heart with a endoscope fitted through the first percutaneous access; creating access to the heart by displacing a pleural sac of the mammal with a pleural sac displacing instrument fitted through the second percutaneous access while observing the heart with the endoscope; creating a third percutaneous access to the mediastinum of the mammal; inserting a flexible endoscope through a first of three lumens of a guiding catheter fitted through the third percutaneous access for observing the pericardium surrounding the heart; placing a suction cup mounted to the distal end of the guiding catheter against the pericardium surrounding the heart; holding the suction cup against the pericardium by evacuating the guiding catheter through the second lumen; cutting an access hole through the pericardium into the pericardial space with a cutting tool deployed from a wire guide fitted through the third lumen; anchoring the distal end of the wire guide in the pericardial space; placing a dilator and sheath into the pericardial space over the guidewire; anchoring the sheath in the pericardium; removing the dilator and guidewire; advancing an electrical lead through the sheath so that the distal end of the electrical lead is positioned in the pericardial space; and anchoring the distal end of the electrical lead in the pericardial space.

Some patients suffer from a condition known as tamponade, resulting from pericardial effusion. This is a condition of excessive fluid in the pericardial space. Correction of this condition requires that the abnormal volume of fluid must be removed before it smothers the heart to the point that it can no longer pump. Entering the pericardial space with a sharp needle is almost trivial in a patient with a pericardial effusion. However, entering the pericardial space is far from trivial in patients without inordinately large pericardial volumes (serous fluid, blood, etc.). It is certainly desirable to enter the pericardial space without invading the circulatory system so that the complications of tamponade, hemorrhage in general, and infection may be minimized. Therefore, there is a need for methods and systems for safely creating a pericardial effusion so that pericardial access may be safely gained for the purpose of introducing defibrillation leads or other diagnostic or therapeutic devices.

The creation of a pericardial effusion allows access to the pericardial space with a needle in much the same manner as in a pericardial drainage. In a pericardial drainage procedure, a needle is placed percutaneously into the pericardial space. For the placement of pericardial, defibrillation leads, it will be helpful to use a percutaneous introducer sheath. However, there are no introducer sheaths intended for the express purpose of affording percutaneous access to the pericardial space.

The systems and methods of the present invention have the advantage of providing access to the pericardial space with minimal trauma to the patient.

Another advantage of the systems and methods of the present invention is that a traumatic extra-pericardial (outside the pericardium) access is provided for the placement of defibrillation leads on top of the pericardium. When leads are placed extrapericardially, lead anchors must be placed to secure the lead. These anchors may be placed through the pericardium on pleural sacs.

Another advantage of the systems and methods of the present invention is that means are provided to observe a beating heart from the frame of reference of the heart to facilitate the control of surgical instruments used to gain access to the pericardial space.

Yet another advantage of the system and methods of the present invention is that surgical instruments used to gain access to the pericardial space are decoupled from the motion of the beating heart.

Still another advantage of the system and methods of the present invention is that there is provided an instrument for displacing a lung in order to gain visual and instrument access to the heart.

Yet another advantage of the system and methods of the present invention is to provide defibrillation leads that are well suited to percutaneous pericardial placement and attachment.

It is a further advantage of the system and method of the present invention that instruments are provided that permit precisely metered motion relative to the moving surface of the beating heart.

BRIEF DESCRIPTION OF THE DRAWINGS

The following detailed description and the accompanying drawings are provided for the purpose of describing and illustrating preferred embodiments or examples of the present invention. This description and accompanying drawings are intended to elucidate the invention through exemplary embodiments and are not intended to limit the scope of the invention in any way.

DETAILED DESCRIPTION OF THE INVENTION

The following description is of the best mode presently contemplated for practicing the invention. This description is not to be taken in a limiting sense, but is made merely for the purpose of describing the general principles of the invention. The scope of the invention should be ascertained with reference to the appended claims.

At the outset, it is noted that the drawings used herein are not intended to be fully detailed representations of the physiological makeup of a mammalian heart and its surrounding pericardium, or of any other part or tissue location of a mammal. Rather, all of the drawings are presented in a simplified format in order to emphasize the main features and steps of the invention. Most physiological detail has been omitted for clarity. However, it also must be emphasized that the drawings have been selected and designed to provide sufficient detail to enable one skilled in the cardiac medical implantation arts to readily understand and practice the present invention.

Figure 1:
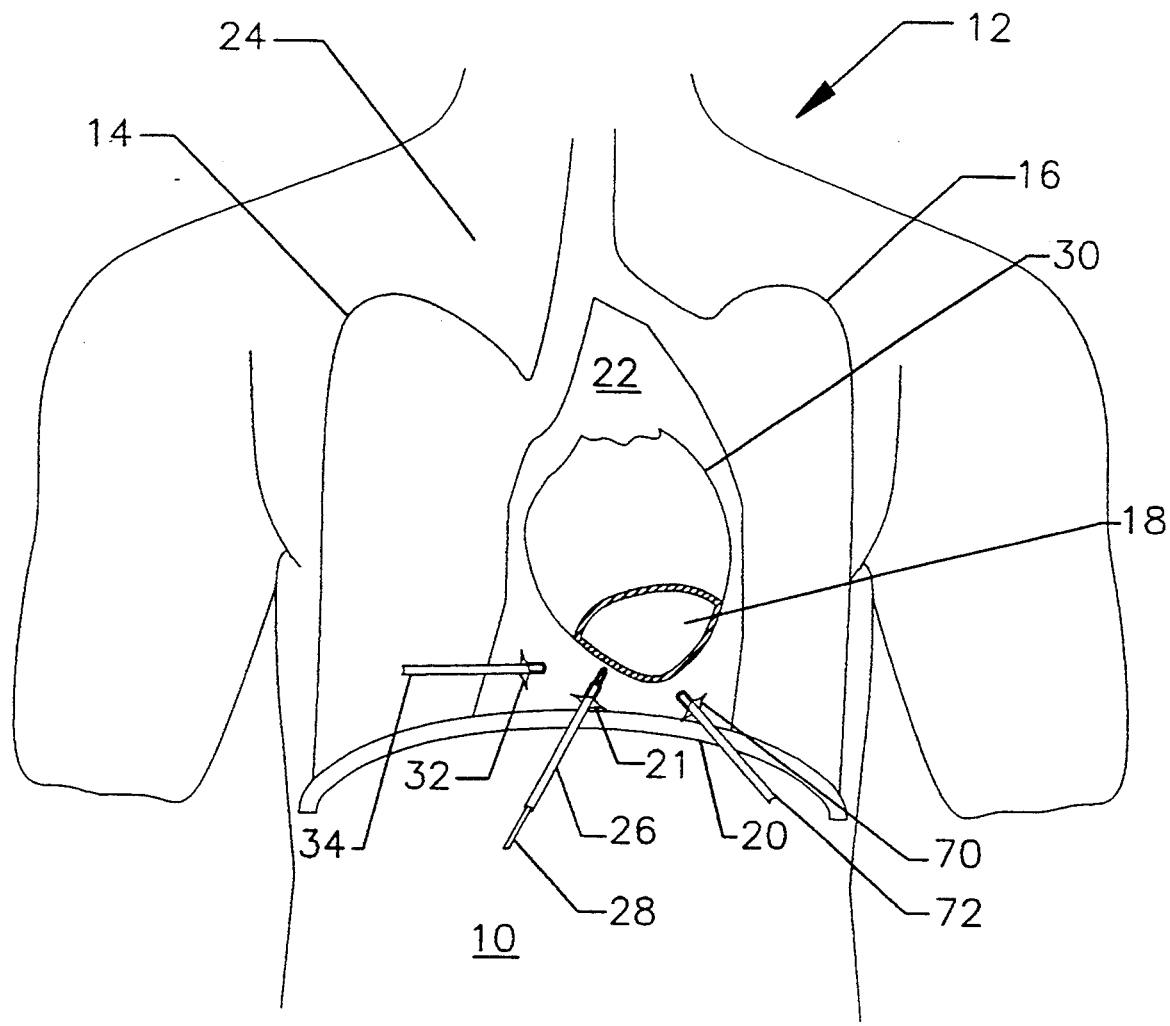
FIG. 1 is a simplified phantom view of the thorax of a human patient showing the heart, diaphragm and lungs.

The present invention provides a method and system for attaching defibrillation leads on or near a beating mammalian heart, as for example, a human heart. Referring now to FIG. 1, there is shown the thorax 10 of a human patient 12, representative of mammals in general. Shown in phantom are the right and left lungs 14 and 16, respectively, as well as the heart 18 and diaphragm 20. The initial step in the process of implanting defibrillation leads in contact with a heart requires that an access hole 21 be cut, preferably through the anterior chest wall 24 of the thorax 10 to create a tract into the mediastinum 22, in accordance with techniques well known by those skilled in the art of thoracic surgery. The mediastinum is the space in the chest between the lungs 14 and 16, around and above the heart 18, bounded in front by the anterior chest wall 24 and in back by the posterior chest and spine, not shown. More preferably, hole 21 is made in a sub-xiphoid location.

A trocar 26 which may have an overall outside diameter of 10 mm, is inserted into the mediastinum through access hole 21. Then an endoscope 28 is inserted through the trocar to observe the heart 18 and lungs 14 and 16. The proximal end of the endoscope 28 is typically connected to a video camera, not shown, to allow real-time observation of the lungs and heart. An important function of endoscope 28 is to provide close inspection of the heart through the translucent pericardium 30 so that a suitable site for implanting the defibrillation leads, not shown, may be identified. However, a broad view of the heart 18 may be obstructed by the lungs. Therefore, unobstructed visual and instrument access to the pertinent regions of the heart may require displacement of one or the other of the lungs 14 or 16. Displacement of a lung may be achieved by creating another access hole 32 through the anterior chest wall 22 to the mediastinum 22 through which a trocar or guiding catheter 34 is placed.

Figure 3:
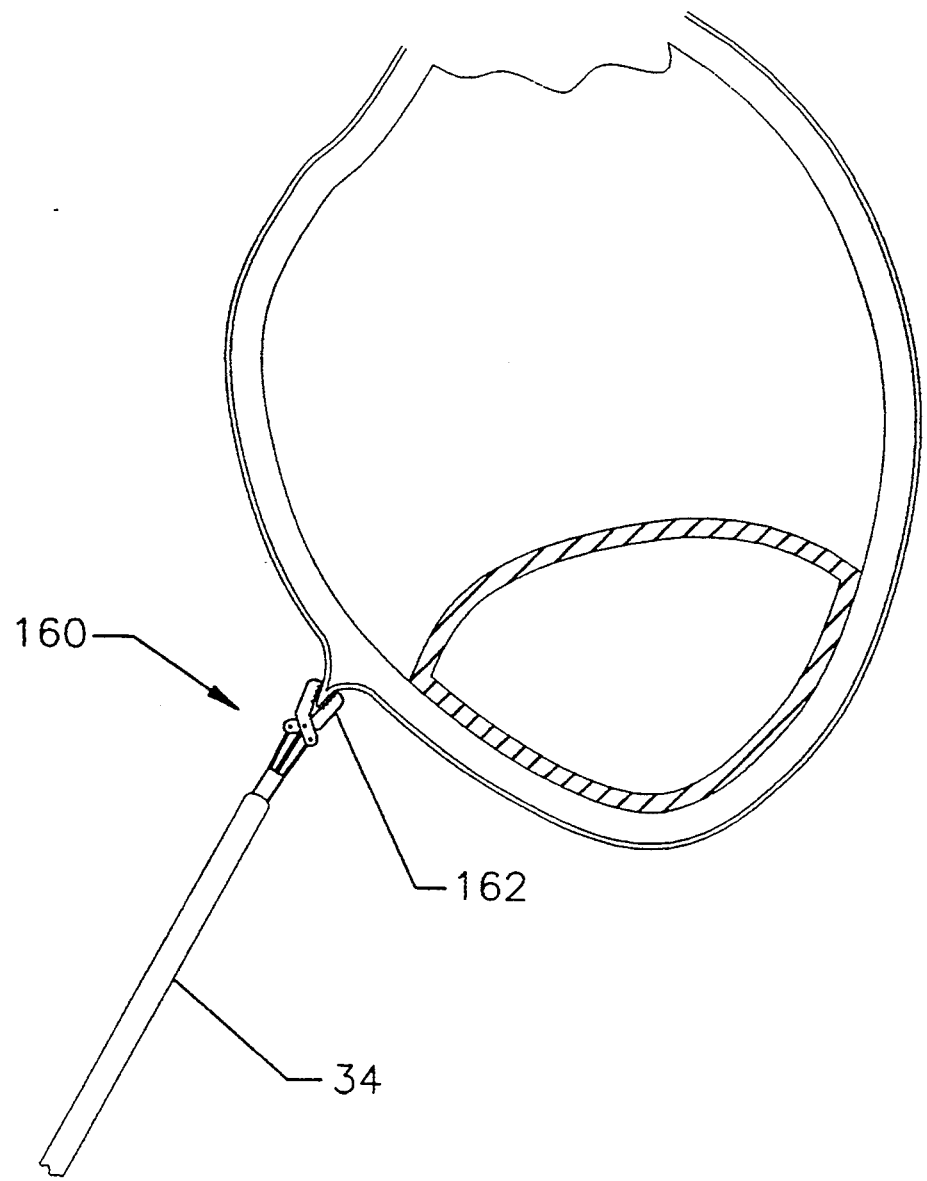
FIG. 3 shows a forceps grasping a pleural sac to retract a lung.

There are several well known ways in which the lungs may be displaced using endoscopic instruments inserted through the trocar or guiding catheter 34. One method of displacing a lung employs endoscopically guided retraction using grasping forceps to pull the pleural sac surrounding one or the other of lungs 14 or 16 away from the pericardium. Referring to FIG. 3, an endoscopic retractor 160 having jaws 162 is inserted into the mediastinum through trocar 34. The retractor 160 is manipulated so that the jaws 162 grasp onto the pleural sac of the lung which is to be displaced. The lung may then be retracted out of the way of the heart 18 by slightly withdrawing the retractor through the trocar 34 or laterally adjusting the retractor position and then holding the trocar in the appropriate position.

Retraction may also be achieved by placing a blunt, soft tipped instrument into the mediastinum and pushing a lung laterally to afford a better view of the heart.

A lung may also be displaced using an instrument having a double walled balloon to gently push the lung.

Figure 4:
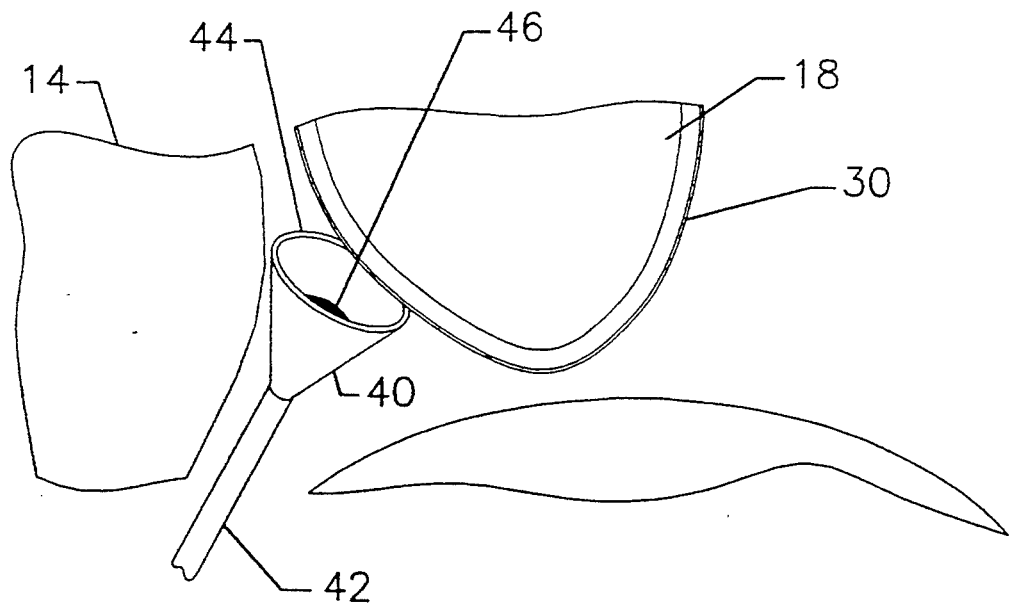
FIG. 4 illustrates an instrument for displacing a lung to provide visual and instrument access to the heart.

Referring now to FIG. 4, there is shown a bell-shaped, double-walled balloon 40 mounted to the distal end of a catheter introducer or guiding catheter 42, positioned in hole 32. When inflated, the wide end 44 of the balloon 40 is positioned so that it rests against the pericardium 30. An aperture 46 in the axial center of the balloon 40 allows another guiding catheter, not shown, to be fitted through the guiding catheter 42 so that the heart may be observed without obstruction from the lungs.

Figure 5:
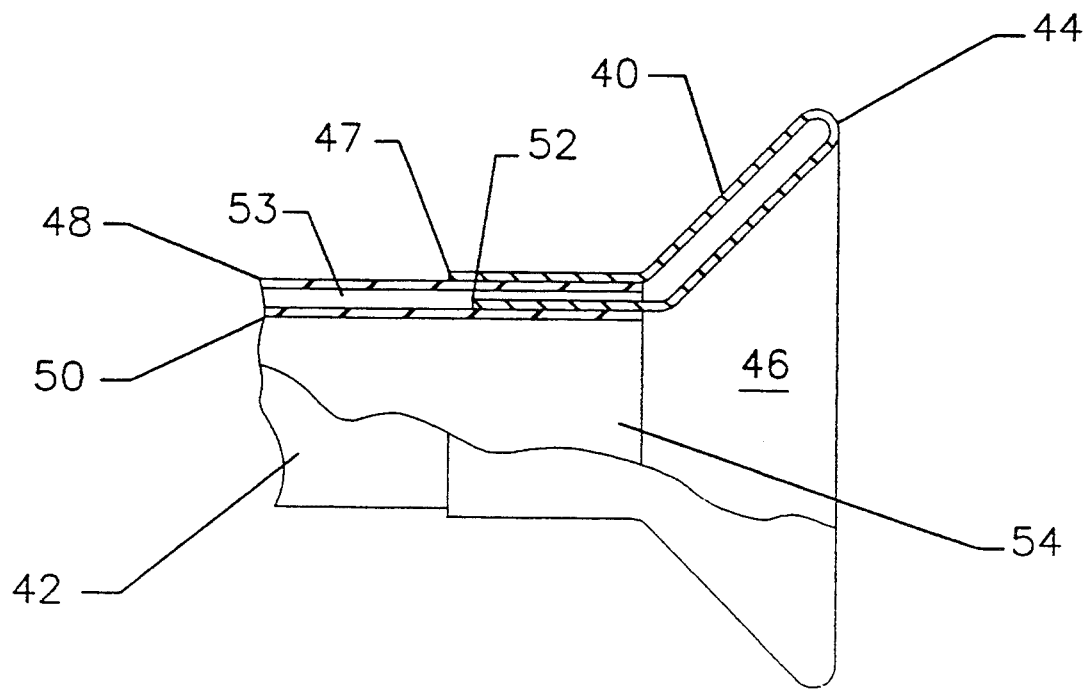
FIG. 5 is a partial cross-sectional view of the bell shaped balloon of the instrument of FIG. 4.

FIG. 5 shows a partial cut-away view of the assembly of balloon 40 attached to the distal end of the catheter introducer 42, where the balloon is shown in the deployed position. Balloon 40, preferably fabricated of a cross linked polyethylene having a wall thickness of about 0.05 mm, or other highly resilient material, and an end 47 attached to the exterior tube 48 of the guiding catheter 42. By way of example, tube 48 may be stainless steel and have an outside diameter of 5 mm and a wall thickness of 0.2 mm. Such attachment may employ an adhesive bond between the balloon material and the exterior of the guiding catheter 42 to provide an airtight seal. Guiding catheter 42 also includes inner tube 50, having an outside diameter, for example, of about 4 mm and a wall thickness of about 0.2 mm, which slides within outer tube 48. End 52 of balloon 40 is attached to inner tube 50, preferably by adhesive bonding. By way of example, tubes 48 and/or 50 may be made of polymeric materials or stainless steel. Methods suitable for attaching the balloon to stainless steel, or to polymeric materials are well known in the field of balloon angioplasty, as for example, heat seals, adhesives or circumferential windings. The through-hole 46 is in fluid communication with the interior of inner tube 50. Pressure to inflate balloon 40 is provided through the annular space 53 formed between tubes 48 and 50 using a Touhy-Borst valve and side arm injector with compressed gland seal, as described in more detail further herein with reference to FIG. 6. A further advantage of the double walled balloon design is that it may be employed as an everting trocar. In other words, with the annular space 53 suitably pressurized the inner tube may be advanced relative to the outer tube. As the balloon everts, it separates the tissue in front of it, much as a toposcopic everting catheter seeks a lumen. In this way access to the mediastinum may be gained quickly and safety as the everting trocar separates muscle layers to find the opening of the mediastinum, and there is no sharp edge to accidently impale the heart.

Figure 6:
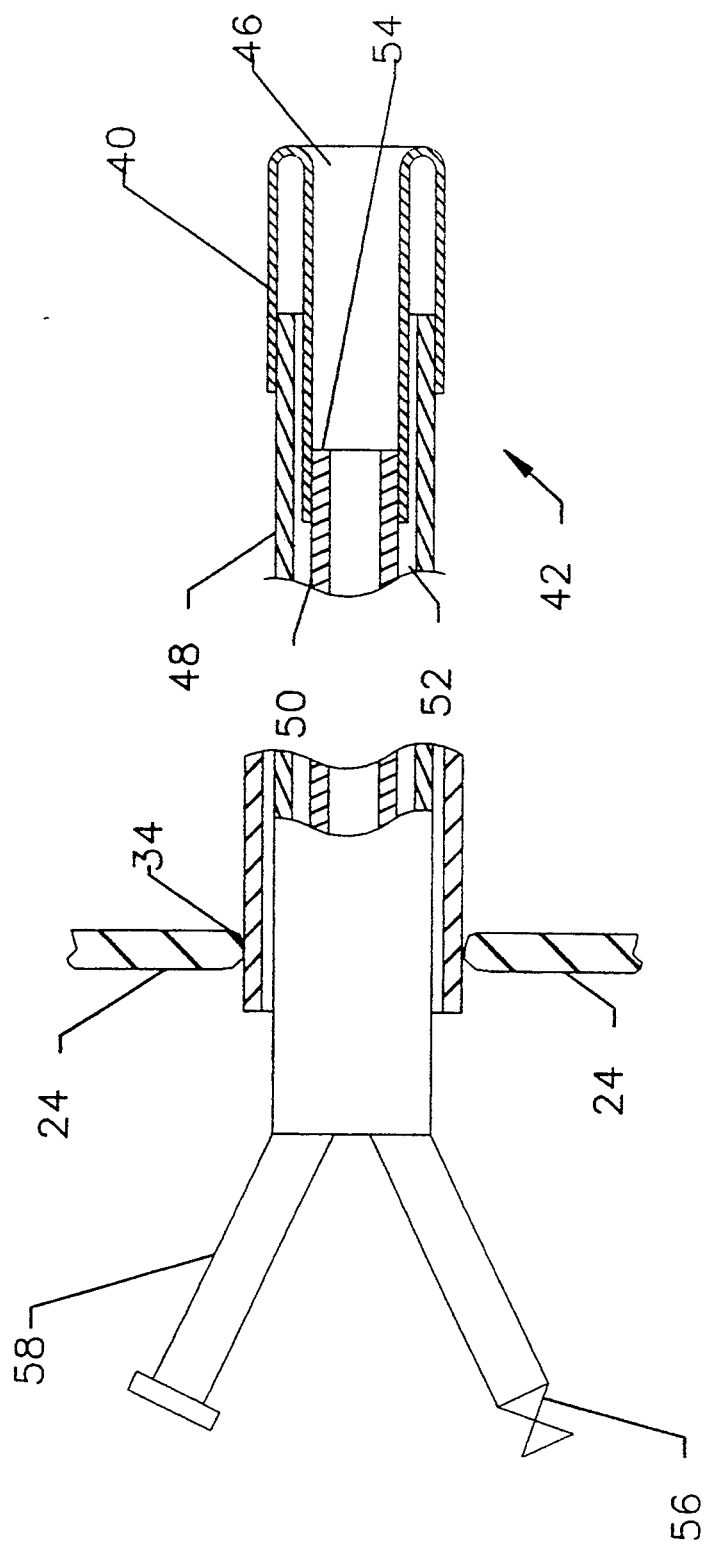
FIG. 6 is a partial cross-sectional view of the instrument for deploying the bell shaped balloon of FIG. 5.

FIG. 6 shows a cross-sectional view of balloon 40 in the retracted position within guiding catheter 42, as the balloon would be positioned when being inserted into the mediastinum. As can be seen, when balloon 40 is in a non-inflated, retracted state, end 54 of inner tube 50 may be positioned within the distal end of outer tube 48. When balloon 40 is in the retracted state, guiding catheter 42 may be inserted into the mediastinum 22 until the balloon 40 is positioned somewhat proximate heart 18.

An everting balloon of any of a variety of shapes may be fabricated for this use. The cone shaped balloon of FIGS. 4, 5, and 6 could be made as indicated in FIGS. 2A and 2B. A polymer material for the balloon is chosen for its ability to be easily formed before being cross-linked. Following cross-linking (induced for example by appropriate exposure to gamma radiation) the material becomes much stiffer and stronger. A piece of polymer (such as polyethylene) balloon tubing as shown in FIG. 2A of a suitable length is expanded to the desired shape while it is still in the raw state. Then it is irradiated to initiate the cross-linking process. The newly shaped and cross-linked balloon then is attached to the inner tube at one end (the smaller end), then neatly creased, partially inverted, and then attached to the outer tube at the other end of the balloon.

Figure 2C:
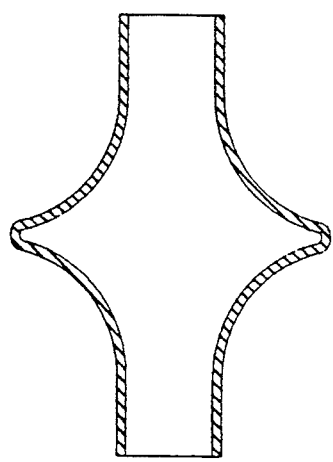
FIG. 2C shows an alternative everting balloon.
Figure 2B:
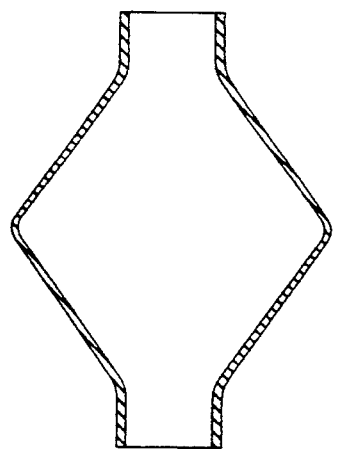
FIG. 2B shows a formed everting balloon.
Figure 2A:
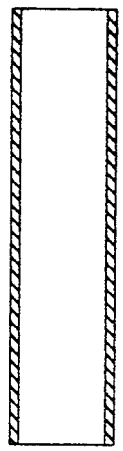
FIG. 2A shows in cross section an unformed everting balloon.

A balloon with a more accentuated distal end may be fashioned as shown in FIG. 2C. The trumpet bell shape of the balloon provides efficient retraction of the lung in the vicinity of the guiding catheter.

Figure 7:
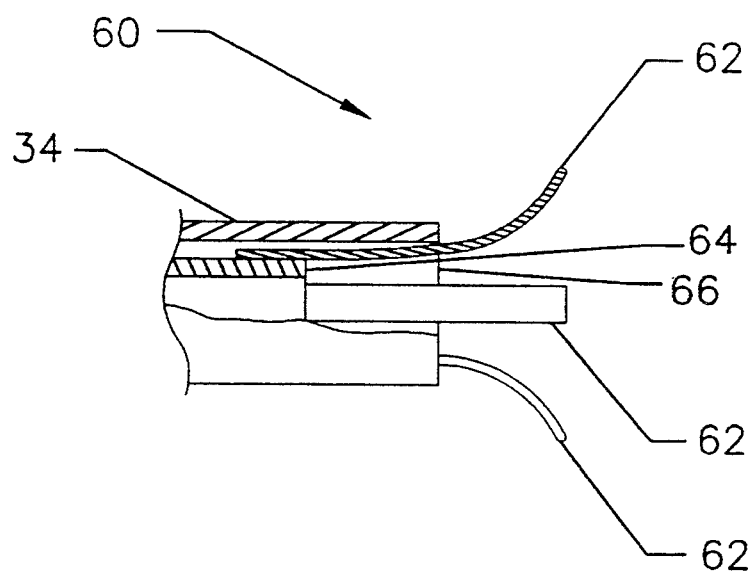
FIG. 7 is a partial, cross-sectional view of another instrument for displacing a lung.

In another embodiment of the present invention, displacement of either of lungs 14 and/or 16 may be effected using a mechanical manipulator 60, as shown in FIG. 7, and employing a set of resilient leaf springs 62 welded circumferentially about the end of a stainless steel inner trocar 64. The steel inner trocar 64 is fitted through the outer trocar 34. Sliding the distal end of inner trocar 64 beyond the distal end of the trocar 34 causes the springs to extend radially outwardly. The leaf springs are preferably manufactured of spring steel and may be encased within a polymeric coating, such as PVC. However, the leaf springs 62 may also made of plastic and be attached to the catheter by an adhesive or a fusing process. In the retracted position, the leaf springs 62 are positioned within trocar 34 until required for deployment. Upon deployment, the inner trocar 64 is pushed toward end 66 of the outer trocar 34 so that the leaf springs extend radially outwardly in a cone-shaped pattern. By way of example, manipulator 60 may include 3 or four leaf springs 62. Coating the leaf springs 62 with a polymeric coating reduces the chance of inadvertently damaging an internal organ, such as the heart or a lung. Furthermore, leaf springs 62 have a spring constant which assures deployment, but which is not so great as to damage the lungs as the springs extend. Displacement of a lung with manipulator 60 may be effectuated by gently pushing the deployed leaf springs against a lung.

Another method for displacing a lung to provide visual and instrument access to the heart is to allow the pressure in the mediastinum to reach atmospheric pressure from its normal negative pressure state, allowing the lungs to shrink. This naturally implies that ventilation would be affected. The pleural space would experience more external pressure than the vacuum to which it is accustomed. Pressurization of the mediastinum could impede ventilation, requiring special attention by an anesthetist.

Figure 8:
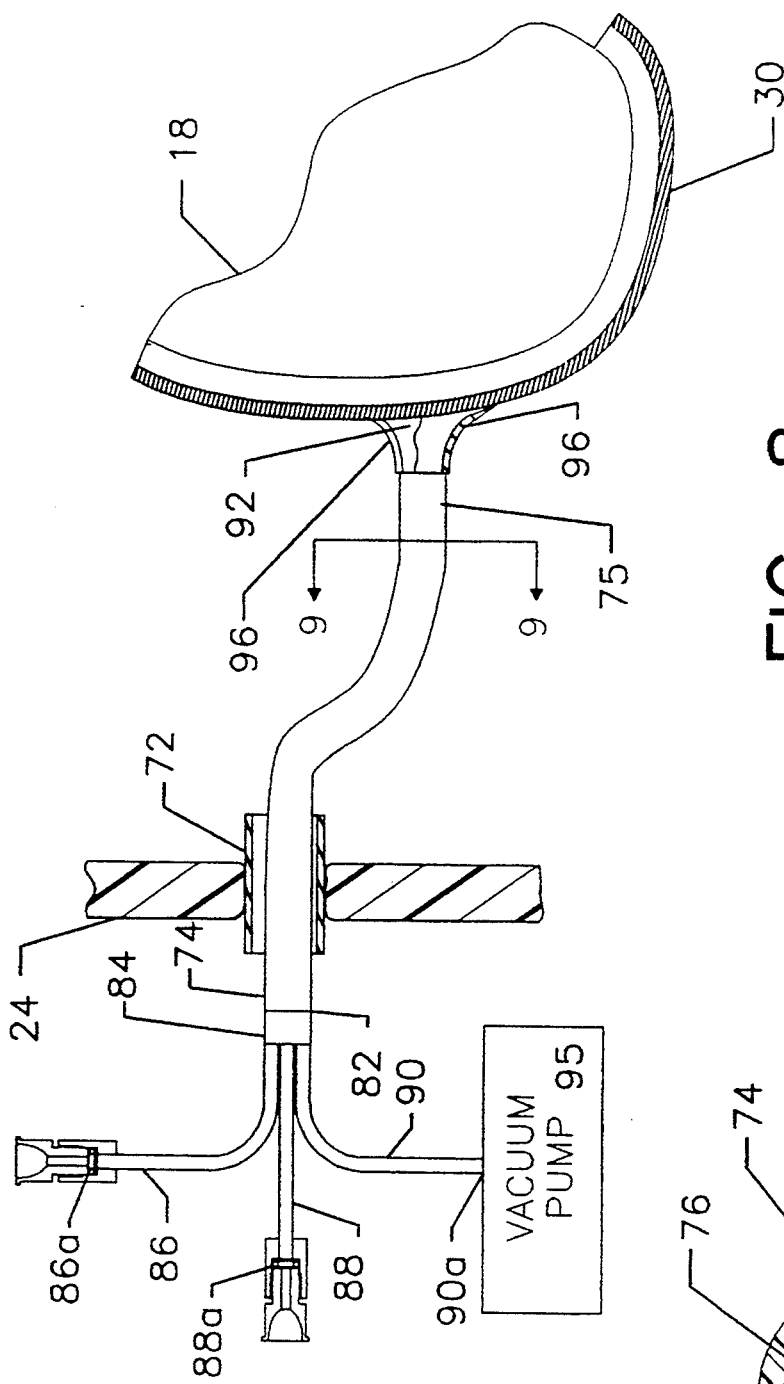
FIG. 8 is a diagram of a guiding catheter held to the heart.
Figure 9:
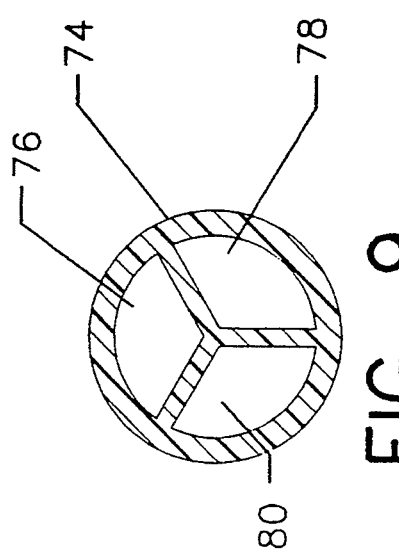
FIG. 9 is a cross-sectional view of the guiding catheter of FIG. 8.

Once access to the mediastinum is established and there is an unobstructed view of the heart using endoscope 28 positioned within trocar 26, a third mediastinal access hole 70, as shown in FIG. 1, is made through the anterior chest wall 24. Access hole 70 is preferably located between holes 21 and 32 through the anterior chest wall 24. The third access hole 70 provides access for instruments which are used to cut through the pericardium and to insert the defibrillation leads or their anchors into the pericardial space 30. The positioning of some of these instruments may be conveniently observed using endoscope 28. Another trocar 72 is inserted through the hole 70 to provide further percutaneous access to the mediastinum. A flexible guiding catheter 74, described below with reference to FIG. 8 is inserted through trocar 72. The guiding catheter 74 is preferably manufactured of a flexible material, such as PVC, and may have an outside diameter of about 3 mm and an outer wall thickness of 0.2 mm. Catheter introducer 74, as shown in cross-section in FIG. 9, preferably includes at least three lumens 76, 78, and 80. The proximal end 82 of the catheter introducer 74 is attached to a manifold 84 having, by way of example, three access ports 86, 88, and 90, each having a seal 86a, 88a, and 90a, respectively. Seals such as O-Rings, Duckbill and compressed gland seals are well known in the catheter field and provide access to the lumens of the guiding catheter 74 in a manner in which the lumens are sealed from the surrounding atmosphere.

Figure 10:
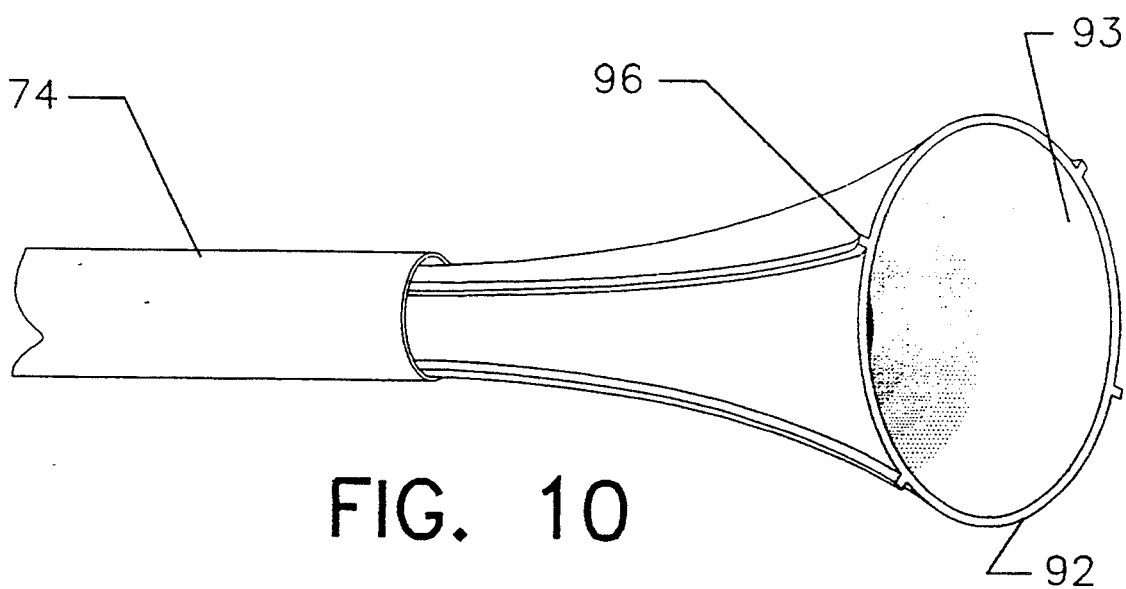
FIG. 10 is a perspective view of a suction cup attached to the distal tip of the guiding catheter of FIG. 8 deployed from a trocar.

As shown in FIG. 8, a somewhat resilient bell-shaped suction cup 92 having a generally conically shaped aperture 93, shown in FIG. 10, is mounted at the distal end 75 of catheter introducer 74 with an airtight seal. Suction cup 92 facilitates safe and reversible attachment of the guiding catheter 74 to the pericardium 30. The suction cup 92 is preferably molded of a resilient material such as a latex rubber, silicone, or other elastomer, which may be glued to the distal end 75 of the catheter introducer 74. Preferably, suction cup 92 is molded from a transparent material so the endoscope 28 (FIG. 1) can also view on the area and help illuminate the pericardium. The suction cup 92 is shown in the deployed state engaged to the pericardium 30, surrounding heart 18, by suction provided by suction means, such as a vacuum pump 95, in fluid communication with access port 90 and lumen 80. Suction applied to the suction cup 92 by vacuum pump 95, as shown in FIG. 8, provides negative pressure between the suction cup 92 and the pericardium 30 which secures the suction cup to the pericardium surrounding the beating heart.

FIG. 10 shows a perspective view of suction cup 92 fully deployed from a trocar 72. Convolutions formed in the suction cup 92 allow the suction cup to be folded in a generally tubular shape so that it may be fitted through the trocar 72.

Figure 11:
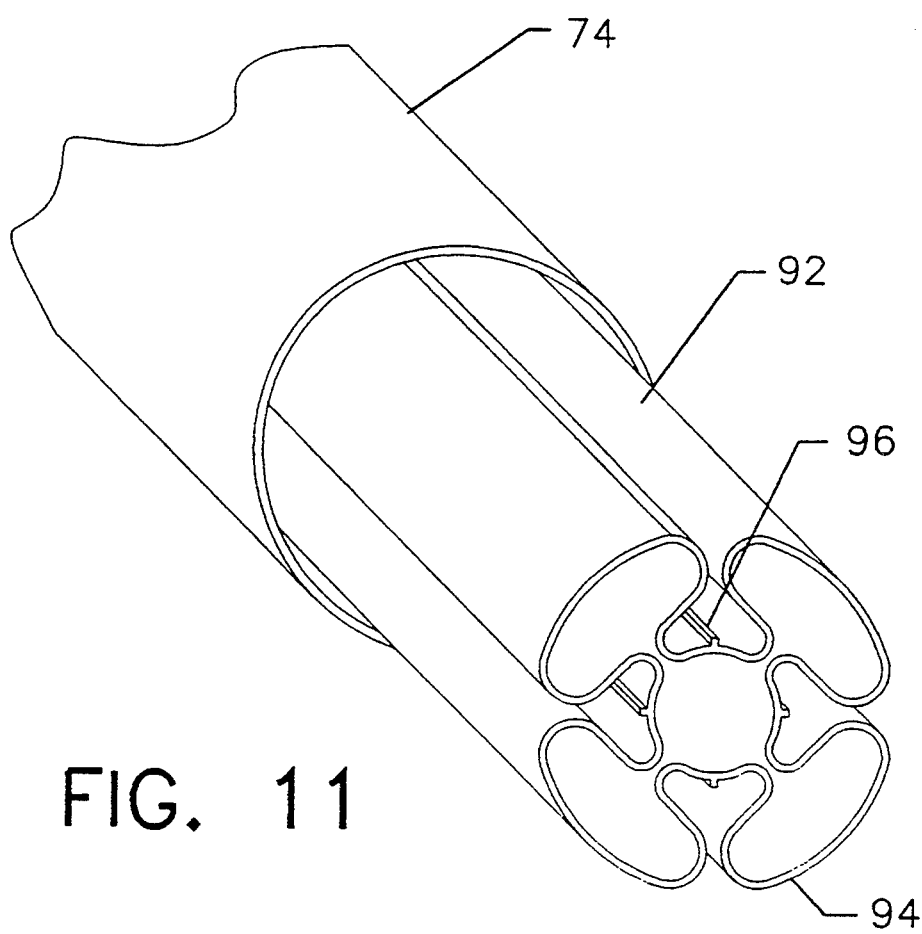
FIG. 11 is a perspective view of the suction cup of FIG. 10 prior to deployment.

FIG. 11 shows a perspective view of the end of the suction cup 92 having relatively thin wall sections 94 in the regions where the suction cup 92 is folded. Suction cup 92 also includes stiffening ribs 96 radially distributed around the outside periphery of the cup to provide stiffness when the cup is deployed.

Referring again to FIG. 1, endoscope 28 is employed to inspect the heart 18 through the pericardium 30 in order to locate a suitable pericardial stick site. The characteristics of a good site are: 1) a dearth of coronary vessels; 2) few, if any, adhesions between the pericardium and myocardium (surface tissue of the heart); and 3) a healthy myocardial appearance. Once a tentative stick site is selected, catheter introducer 74 is inserted through the trocar 72 further into the mediastinum 22 where the suction cup 92 deploys to a bell shape. The trocar 72 is manipulated so that the suction cup 92 abuts against the pericardium, preferably centered around the tentative pericardium stick site. Then the suction cup 92 is drawn through lumen 80 and suction port 90 of the guiding catheter 74 in order to hold the suction cup 92 against the pericardium. An important benefit of the guiding catheter 74 is that it effectively decouples the motion of the beating heart 18 from the cardiac surgeon, making the implantation of defibrillation leads within the pericardial space a much safer procedure than it would otherwise be. The shape of guiding catheter is preformed to allow for flexion as the heart beats, and is cantilevered against the heart to provide an additional spring force to aid in the stabilization of the catheter tip with respect to the beating heart.

Figure 12:
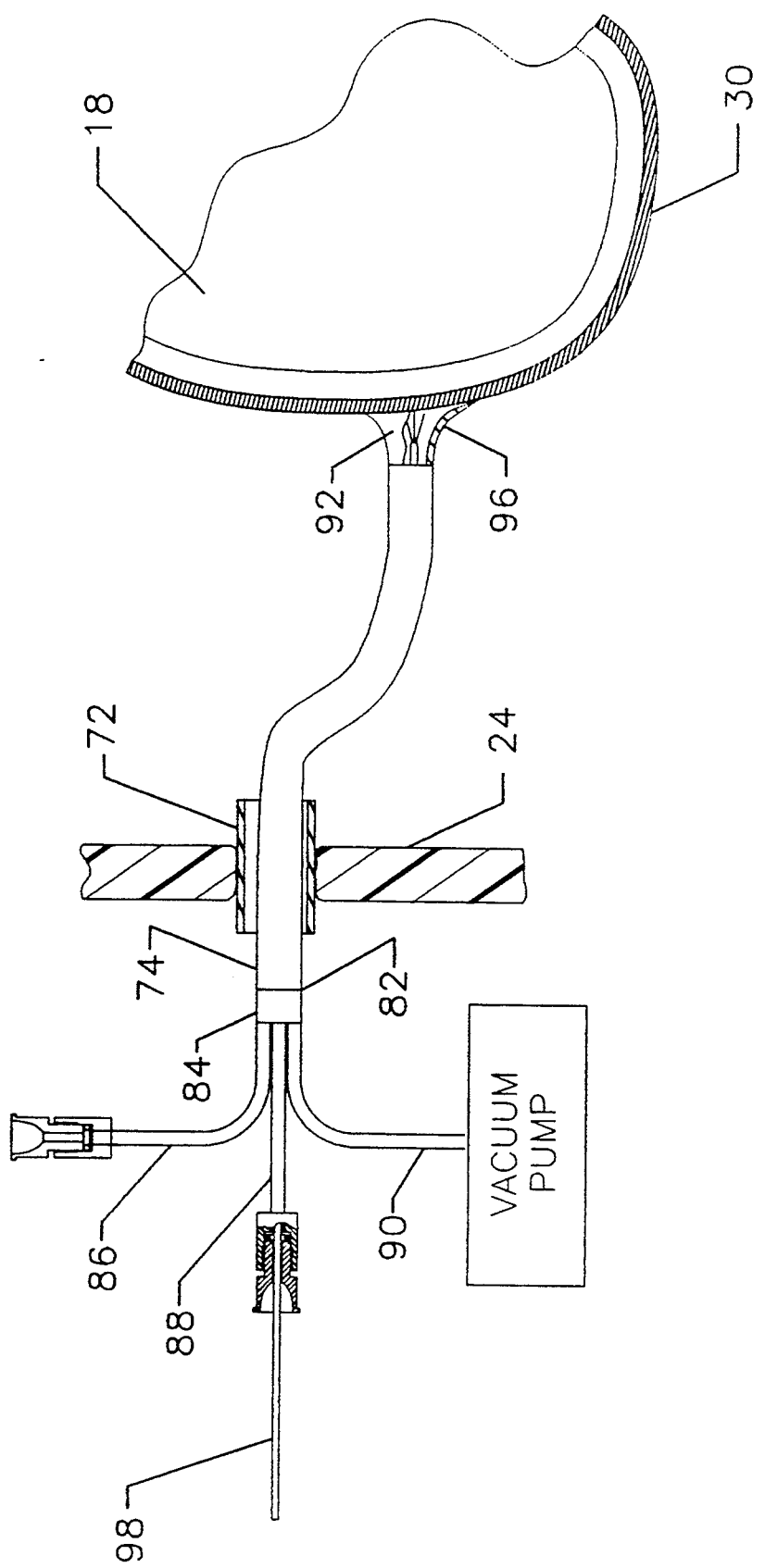
FIG. 12 shows an endoscope deployed through the guiding catheter of FIG. 8 viewing the pericardium.

Next, with reference to FIG. 12, the surgeon affirms that the tentative pericardial stick site is indeed a good location through which to insert or anchor the defibrillation leads. Such affirmation is achieved by inserting a flexible endoscope 98 through port 88 and lumen 78 of the catheter introducer 74 so that the surgeon can inspect the pericardium through aperture 93 of the suction cup 92. Endoscope 98 passes through a compression gland seal, not shown, in port 88 of manifold 84, as is well known by those skilled in the art. Once the pericardium stick site is verified, a cutting instrument for penetrating the pericardium 30 is inserted through port 86 and lumen 76 of the guiding catheter 74. If upon closer examination of the pericardium 30 with endoscope 98, the surgeon decides that the tentative stick site should be changed, the surgeon may relocate the suction cup 92 to a new location on the pericardium and verify a new stick site.

Figure 13:
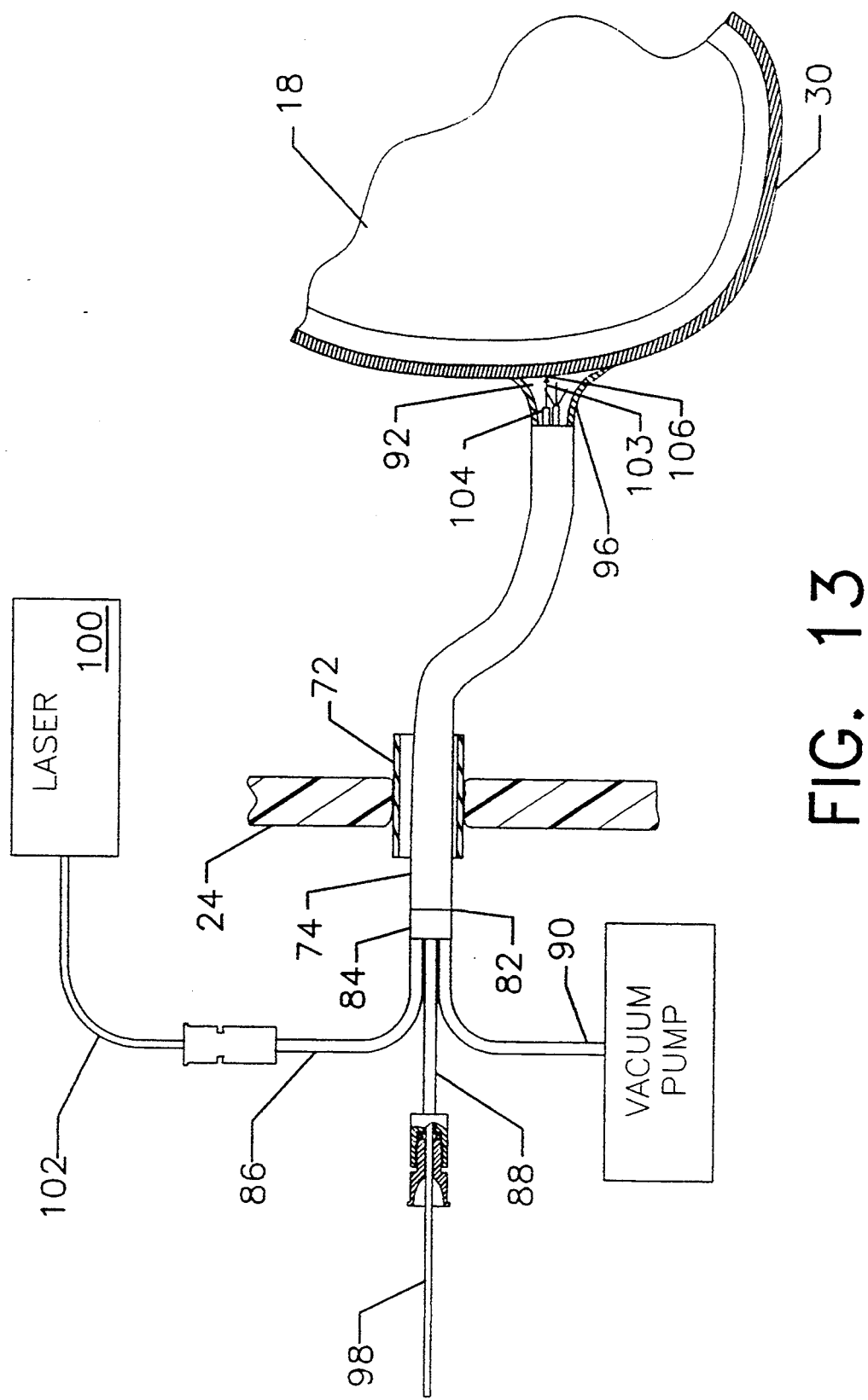
FIG. 13 shows a laser system for cutting through the pericardium which includes a fiber optic channel deployed through the guiding catheter.

The next step after verifying a pericardial stick site, is to insert an instrument into the mediastinum through lumen 76 that is capable of cutting a hole through or perforating the pericardium 30. One method for cutting a hole may employ laser radiation to irradiate and penetrate the stick site. Referring to FIG. 13, a pulsed laser 100, such as an excimer laser which can produce shallow, clean cuts in tissue, is optically coupled to an optical fiber 102 advanced through lumen 76 of guiding catheter 74. The laser fiber is advanced so that it is in the field of view of the miniscope 98 which provides visual feedback of the laser energy 103 cutting through the pericardium at the stick site 106.

Figure 14:
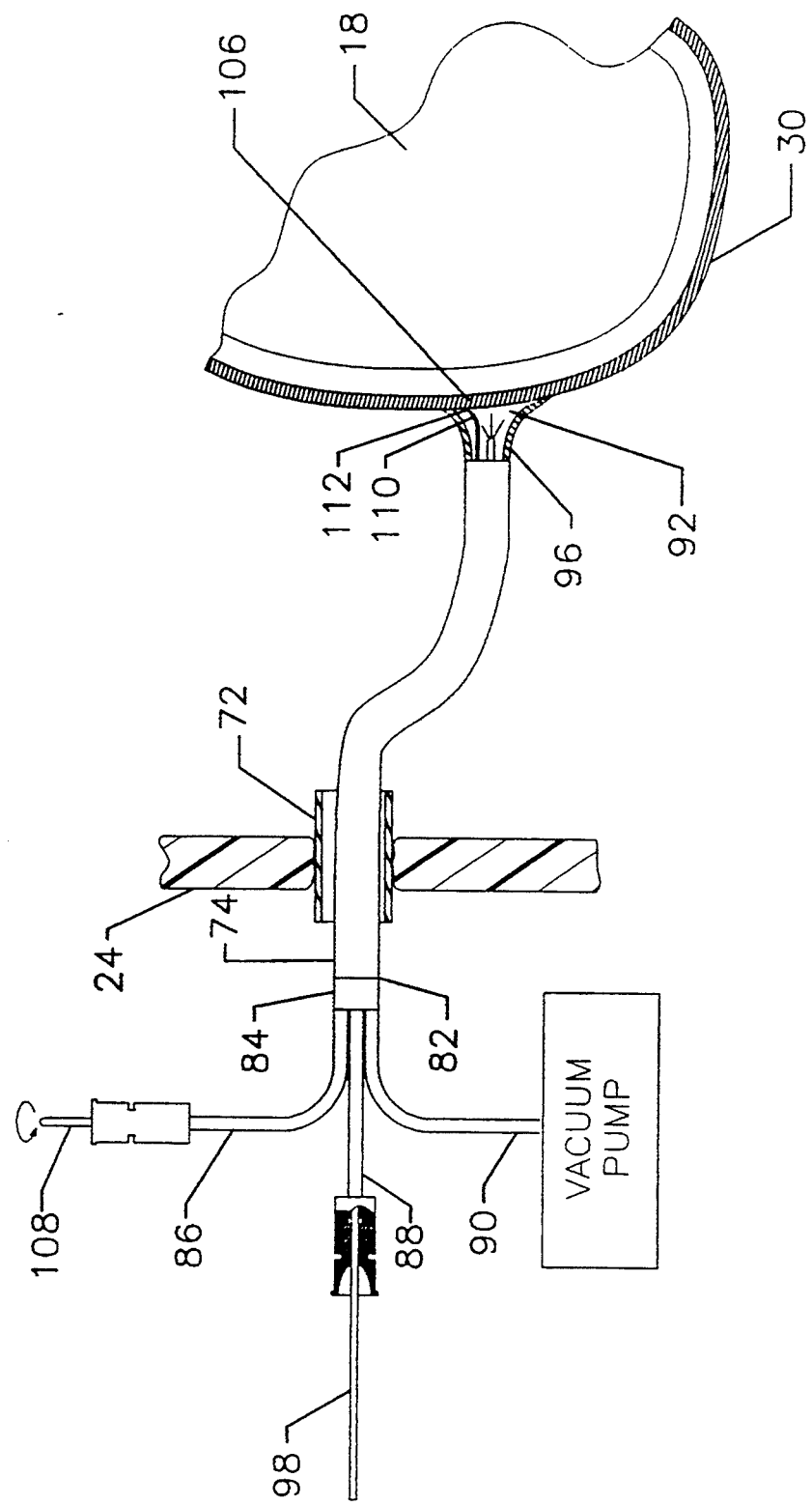
FIG. 14 shows a retractable cutting needle deployed through a flexible wire guide and the guiding catheter for cutting access to the pericardial space.

An alternative to using a laser for creating a hole through the pericardium employs a wire guide including a retractable needle tip. Referring to FIG. 14, a flexible guidewire 108 is fed through port 86 of manifold 84 and through lumen 76. The guidewire 108 has a deflectable end 110 which allows the end to be precisely positioned against the pericardial stick site 106. Also referring to FIG. 15, a retractable needle tip 112 positioned within wire guide 108 may be extended a predetermined distance beyond the blunt end cap 114 at the distal end of the wire guide 108 through an aperture, not shown. Tension applied to the activation wire 120 at the proximal end of wire guide 108 translates the end 110 of wire guide 108 in an arc, causing needle tip 112 to slice the pericardium 30. After cutting a small slice through the pericardium, the needle 112 is retracted.

Figures 15, 16:
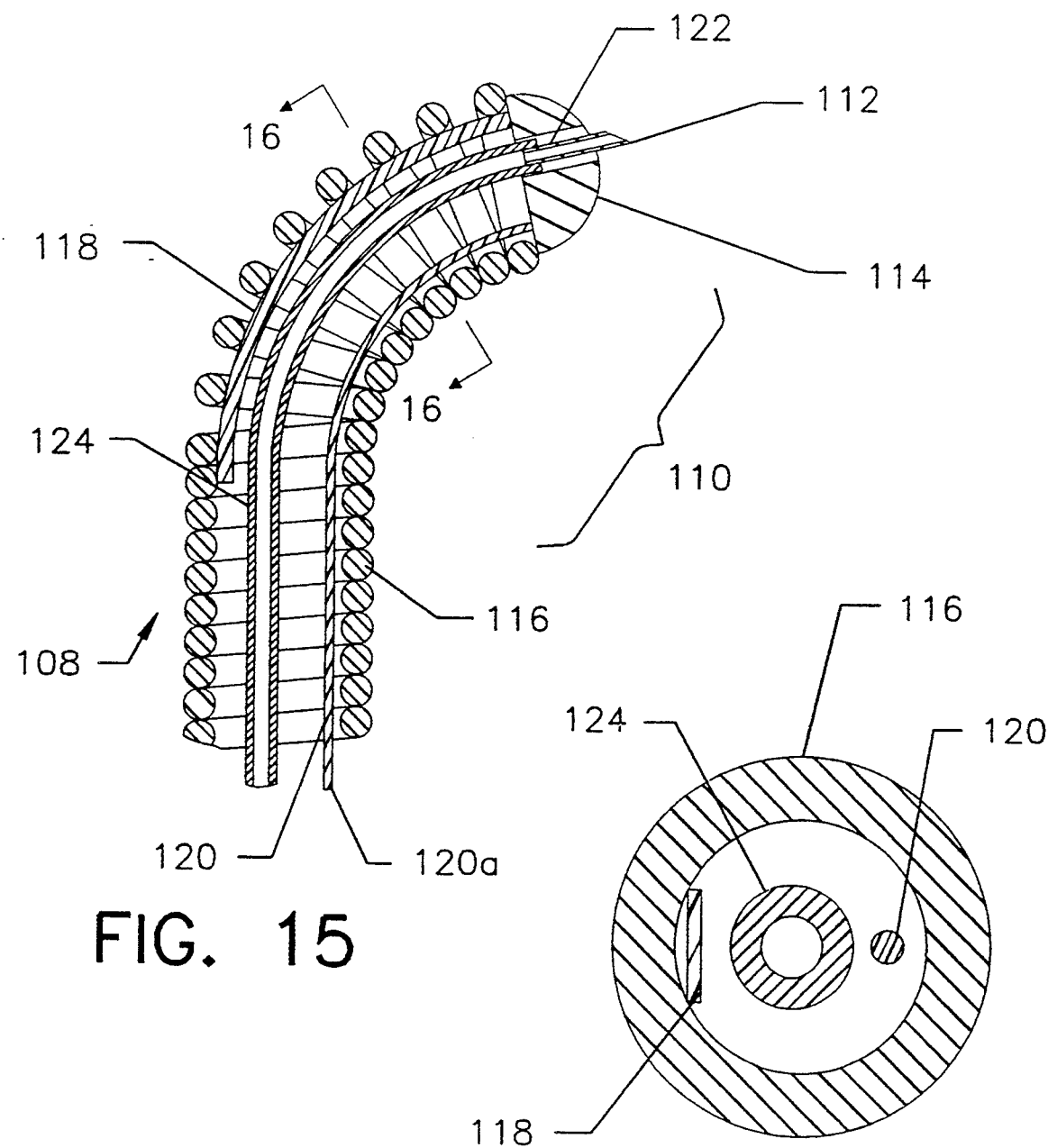
FIG. 15 is a longitudinal, cross-sectional view of the flexible wire guide of FIG. 14.
FIG. 16 is a cross-sectional, transverse view of the flexible wire guide of FIG. 15.

Details regarding the construction of wire guide 108 are described with reference to FIGS. 15 and 16 which depict the blunt distal end 114 of the wire guide. Wire guide 108 is shown to be formed of stainless steel wire 116 tightly wound in a helical coil. The helical coil provides the wire guide 108 with good flexibility and column strength. One side of the interior region formed by the coiled wire 116 includes a weld bead, or wire, 118 running along the longitudinal length of the tip deflecting portion of the wire guide. The welded wire 118 stiffens one side of the wire guide 108 with respect to the opposite side of the wire guide. Opposite the welded stiffener wire 118 in the interior of the wire guide 108 is an activation wire 120 welded only at the distal end 110 of the coiled wire 116. The actuation wire 120 runs along the length of the wire guide and has a section, 120a extending beyond the proximal end 122 of the wire guide. A hollow needle 122 having a tapered distal tip is attached to a flexible tube 12A within the guidewire body and also runs through the entire length of the wire guide 108. The needle tip 112 at the end of needle 122 is tapered and very sharp. By way of example, coiled wire 116 may be formed of stainless steel wire having a diameter of 0.1 mm. The needle 122 may be manufactured of stainless steel tube having an outside diameter of 0.3 mm and a wall thickness of 0.05 mm. The flexible needle body may be formed of polyurethane and have an outside diameter of 0.5 mm with a wall thickness of 0.1 mm. The distal end 110 of the wire guide is deflected by pulling on the end 120a of the activation wire 120, causing the needle tip 112 to be dragged along the pericardium, thereby slicing it in order to gain access to the pericardial space 109. After slicing the pericardium, the needle tip 112 is retracted within the needle guide 124.

The pericardium may also be cut using cutting tools, such as flexible forceps inserted through the lumen 76 of the guiding catheter 79. Such forceps are well known by those skilled in the art of laproscopic surgery.

Figure 17:
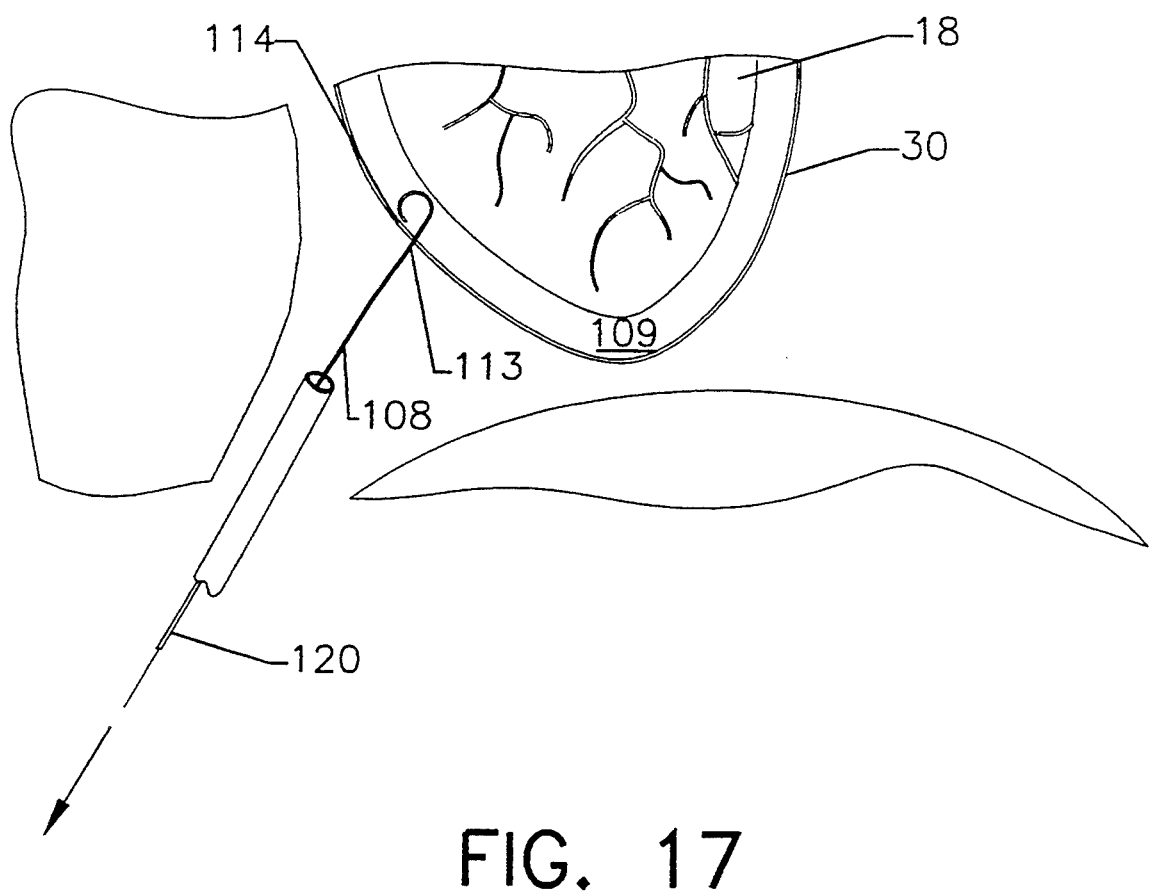
FIG. 17 shows the distal end of the wire guide, with the needle in the retracted position and the tip deflected in a "J"-shape.

The distal end 110 of wire guide 108 remains situated by the access hole 113 cut by the needle tip 112. The wire guide 108 is advanced through the hole 113 so that the end 110 of the wire guide 108 further penetrates into the hole sliced through the pericardium 30. Next, tension applied to wire 120 deflects the end 110 of wire guide 108 into a "J" shape, as shown in FIG. 17 so that the end 110 of the guidewire 108 is prevented from becoming dislodged from the pericardial space 109. Once the end 110 of the wire guide 108 is secured in the pericardial space 109, the handle is detached and the guiding catheter 74 is withdrawn from the mediastinum, leaving the wire guide 108 in place.

The activation wire 120, the helical spring 116, and the flexible tube 124 are all attached to a detachable guidewire handle, described below with reference to FIG. 23. The handle controls deflection, retraction of the needle tip and infusion. The handle is detachable so that the guidewire catheter may be removed. The guidewire body includes a detent mechanism small enough to fit through the lumen of the guiding catheter 74. The detent holds the tip of the guidewire in the deflected position so that the guidewire remains deflected (and so safety anchored in the pericardium) while the handle is detached. The detent may consist of a cantilever spring assembly mounted to the activation wire. When the activation wire is pulled, the detent springs out of the confines of the guidewire body and prevents the activation wire from sliding forward and allowing the guidewire tip from straightening (until the detent is manually depressed).

Figure 23:
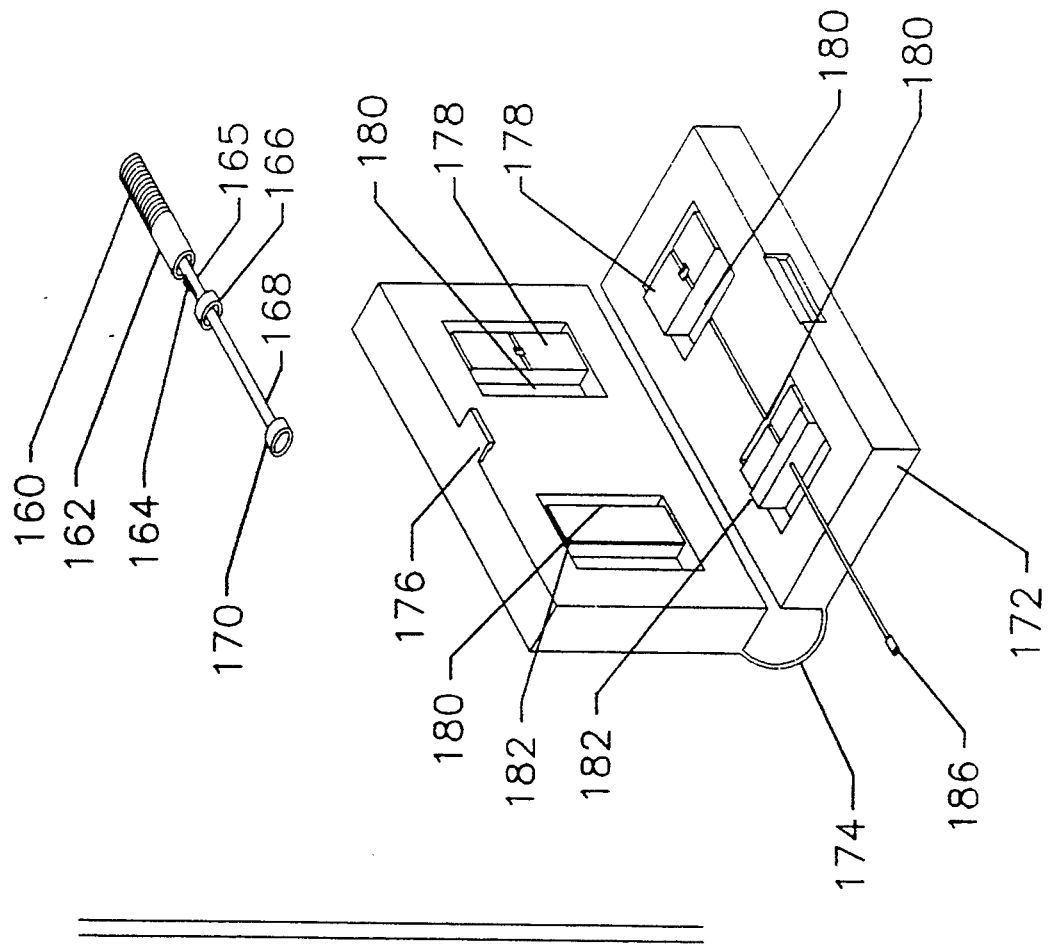
FIG. 23 shows the proximal end of the guidewire and the detachable handle which controls it.
Figure 23:
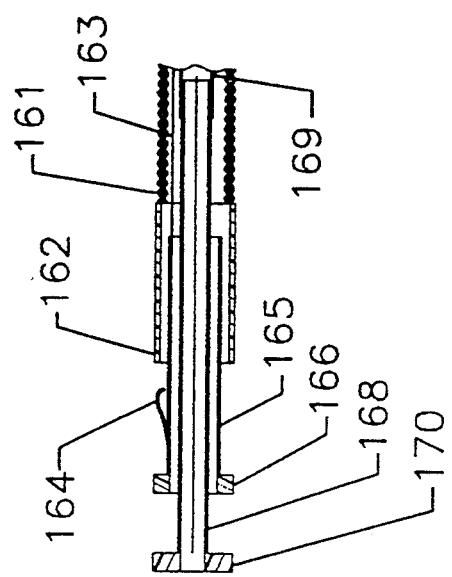

With reference to FIG. 23, an exemplary embodiment of a detachable guidewire handle is described. The helical coil 161 of guidewire 160 is terminated at a fitting, hypo tube 162. The activation wire 163 is terminated and attached to tube 165. A portion 164 of the tube 165 is bent away from the center and acts as a spring loaded detent to hold the tip deflection by maintaining tension in the activation wire 163. As soon as the guidewire is removed from the handle, the detent is free to spring outward. When placed back in the handle, the detent is pressed inwardly so that the guidewire tip may be straightened.

The handle consists of a body 172 composed of two halves connected by a living hinge 174. The two halves may be snapped together using latch 176. The deflection is controlled by manipulation of a slide lever (not shown) connected to the activation wire 163 indirectly by trapping tube 166 between grippers 178. Tube 166 is connected to the activation wire and tube 165.

Control of the axial position of the cutting needle at the distal guidewire tip is done by manipulating a slide lever (not shown) on the handle body. The lever is connected to tube grippers 182. The tube grippers 182 include resilient surfaces 184 to promote effective sealing to the tube. Tube 168 is a hypo tube which is connected to the flexible tubing 169 within the guidewire, which in turn is connected to the sharp needle tip. Fitting 170 is provided at the termination of tube 168 to promote effective seal formation to the handle grippers 182. Infusion through the guidewire may be accomplished through lever hub 186.

Figure 18:
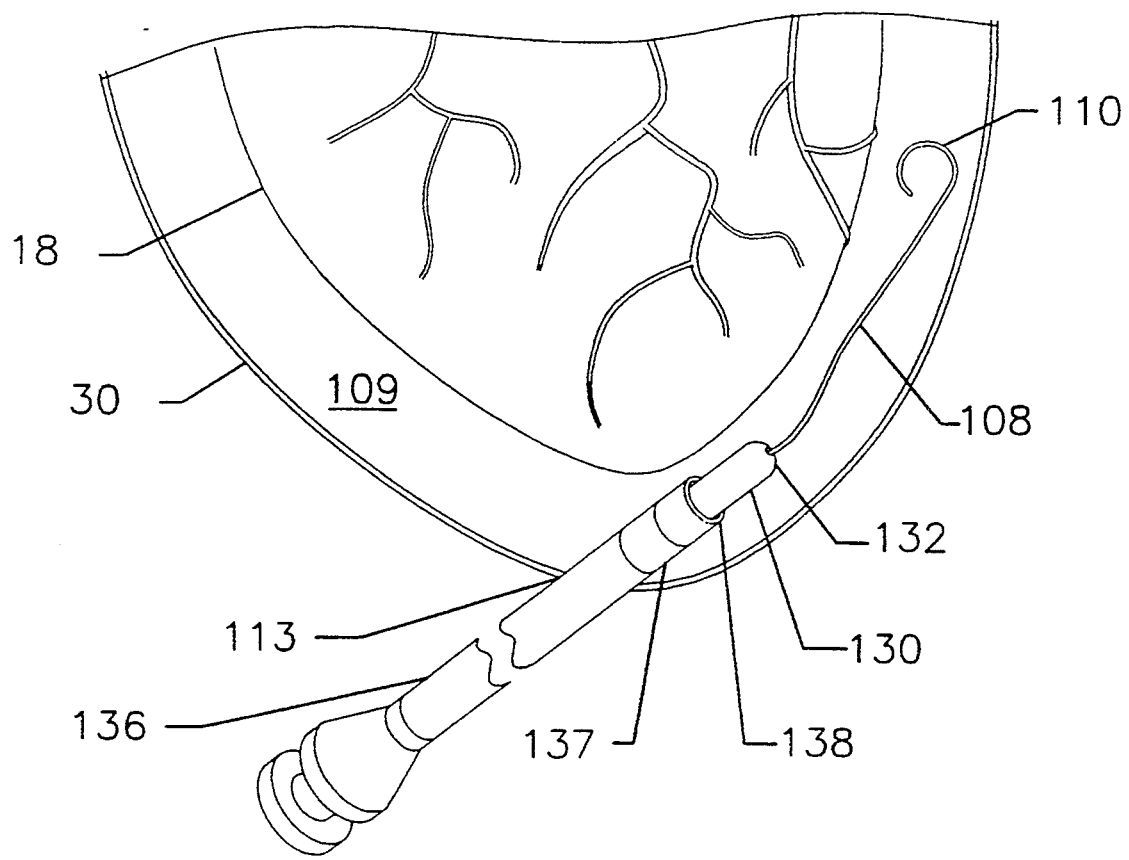
FIG. 18 shows the dilator and sheath fitted over the guidewire and penetrating into the pericardial space.

Referring to FIG. 18, a flexible, dilator 130 having a blunt, tapered end 132 and sheath 136 next are slid over the wire guide 108 and advanced into the pericardium. The dilator is preferably formed of a polymeric material, such as polyurethane, and has a bore 134 which provides a generally close, sliding fit over the wire guide 108. For example, the dilator 130 may have a wall thickness of 4.5 mm and an outside diameter of 10 mm. The tapered, blunt-shaped distal end 132 of the dilator, when advanced into the pericardial space 109, dilates the hole 113 previously cut through the pericardium. Increasing the size of the pericardium access hole 113 is desirable in order to facilitate subsequent entry of the defibrillation leads through the hole.

Figure 19:
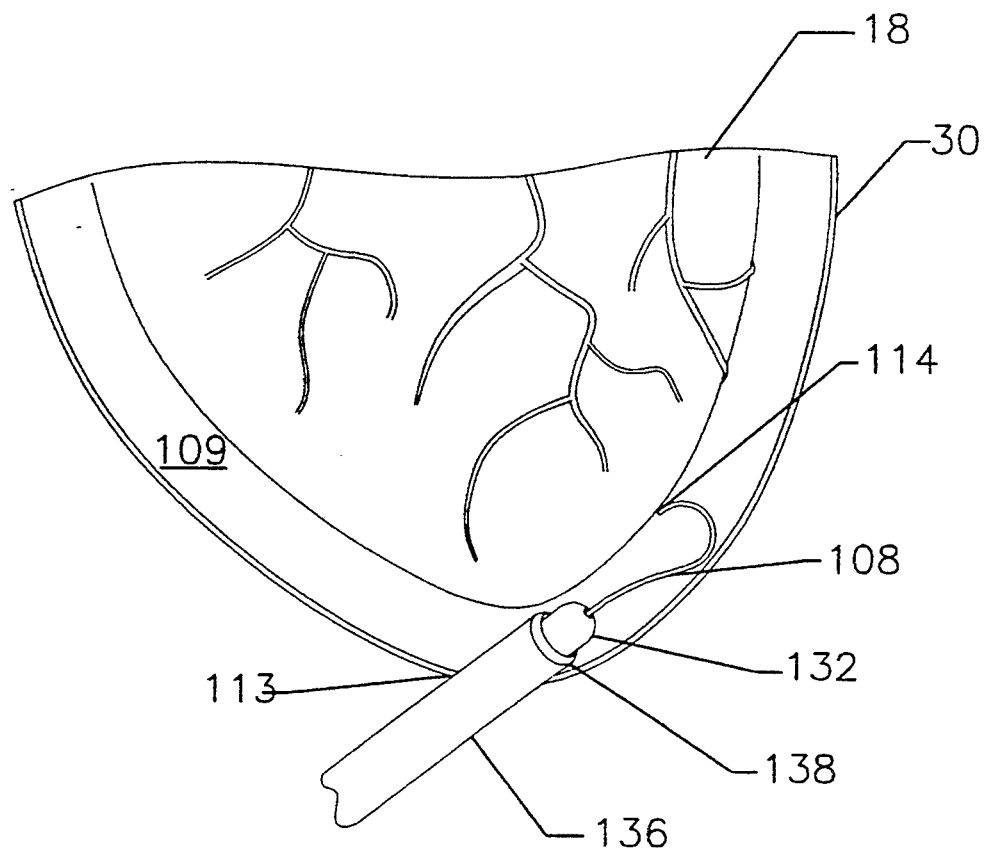
FIG. 19 shows another view of the dilator and sheath.
Figure 20:
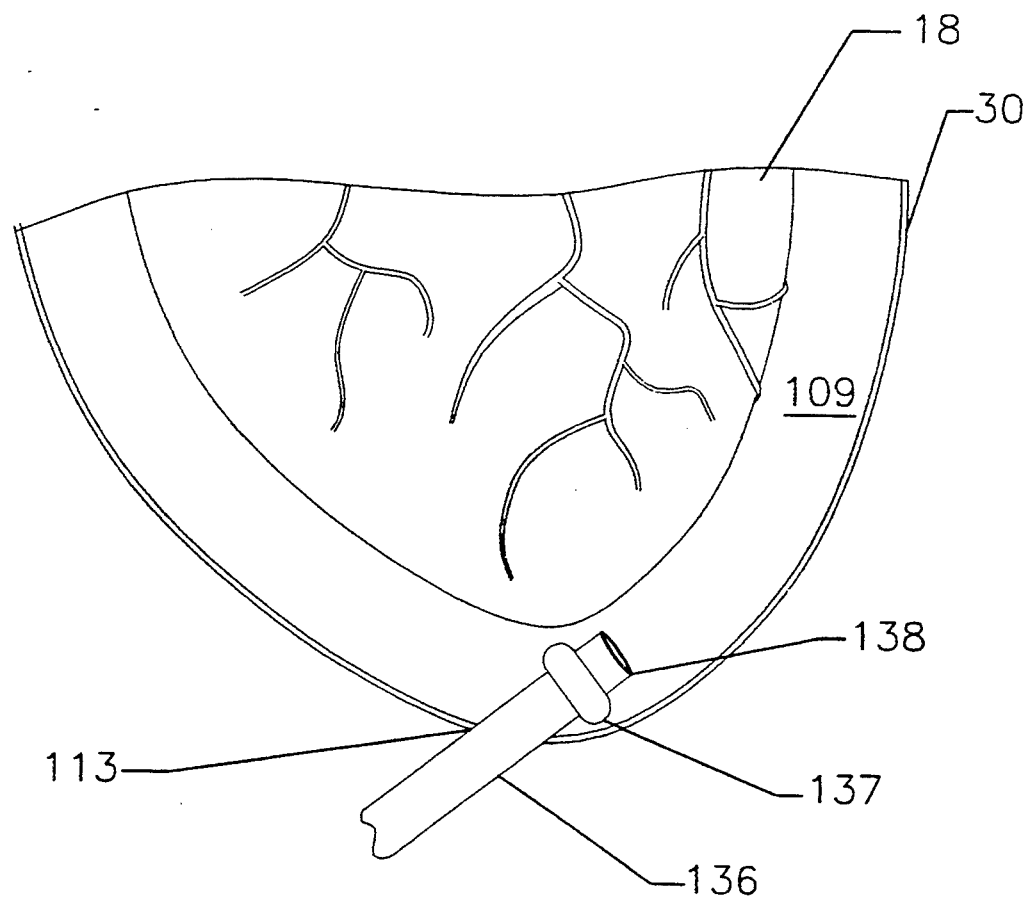
FIG. 20 shows the sheath with its anchor deployed in the pericardial space and with the dilator withdrawn.
Figure 21:
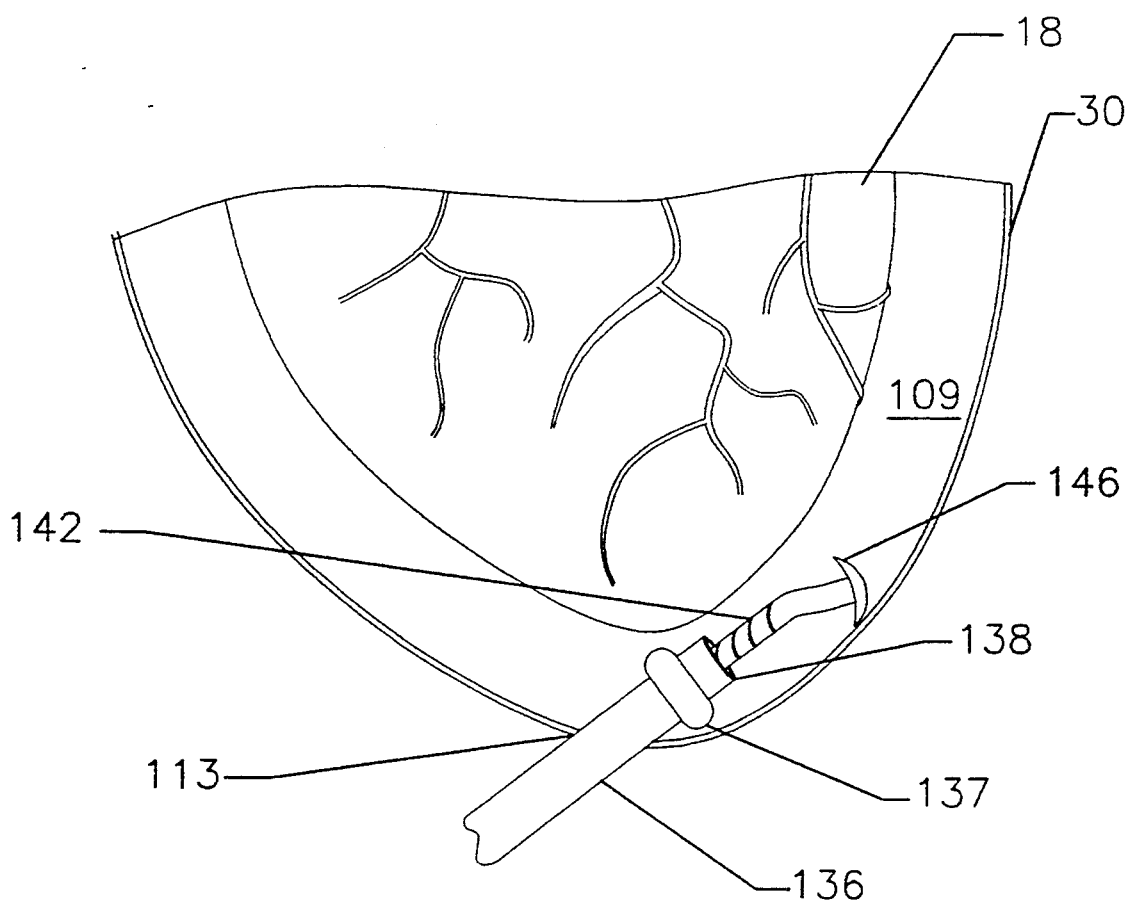
FIG. 21 shows the electrical lead fitted through the sheath.

As shown in FIGS. 18 and 19, after the hole 113 through the pericardium is dilated, the semi-rigid sheath 136 is advanced so that the distal end 138 of the sheath is positioned within the pericardial space 109 and held there by deploying the sheath anchor 137. Then, the dilator 130 is withdrawn, as shown in FIG. 20. A defibrillation lead ("lead") 140, shown in FIG. 21, is advanced through the sheath so that the distal end of the lead is positioned within the pericardial space 109.

Figure 22:
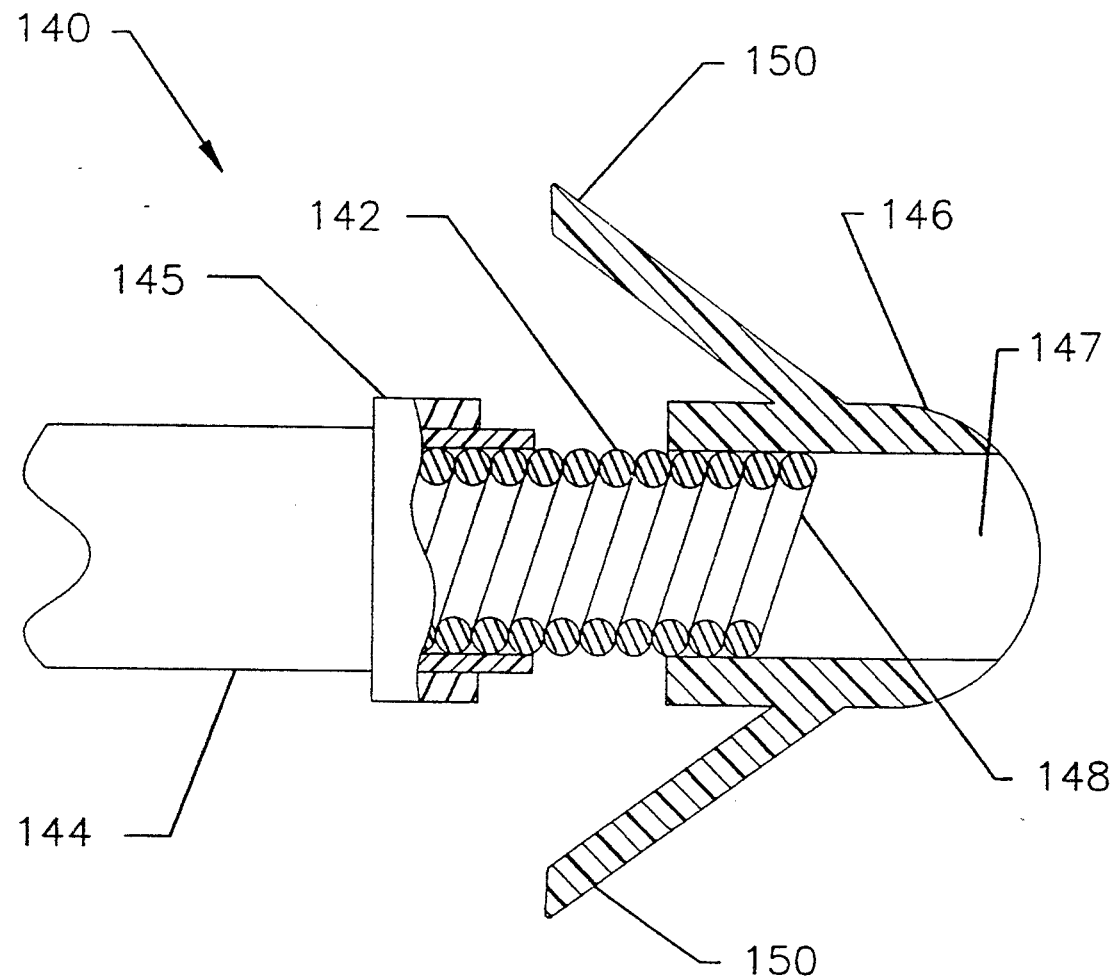
FIG. 22 shows a cross-sectional view of the distal end of the electrical lead.

The lead 140 preferably may be constructed, as shown in FIG. 22, to include helically coiled, electrically conductive lead wire 142 substantially coated with a biocompatible insulator 144, such as polyurethane or silicone, over most of its length. At or near the distal end of the lead wire 142, there will be an electrode which is not coated with insulation. The electrode provides electrical continuity between the lead wire 142 and myocardial tissue, not shown. A blunt-shaped end cap 146 is mounted to the distal end 148 of the lead wire 140 by means which may include well known manufacturing processes, such as crimping, adhesive bonding, or interference fitting. The helically wound lead wire 142 and end cap 146 define a bore 147 sized to easily slide so that the lead may be inserted into the pericardium without placing the sheath. The end cap 146 includes two or more tapered petals, barbs 150 or a flexible flange which allow easy penetration of the end cap 146 through the hole 113 leading into the pericardial space 109, but which resist withdrawal of the end cap 146 back out of the hole. Thereby, the distal end of lead 140 is secured in the pericardial space 109.

A lead placed extrapericardially may be anchored near the heart by placing one or more "passive" anchors within the pericardial space. A lead placed within the pericardium may be anchored securely in place by positioning the lead tip and electrode within the pericardium and piercing the pericardium from the inside to place the anchor extrapericardially.

Figure 25:
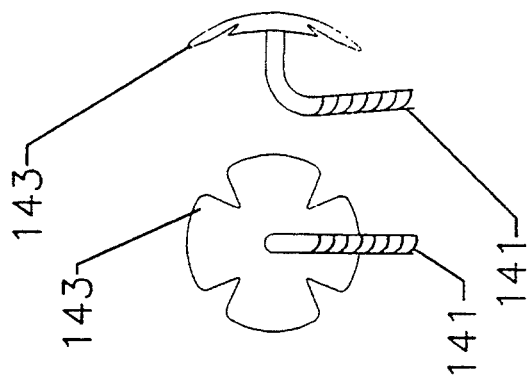
FIG. 25 shows orthographic views of the lead anchor.
Figure 24:
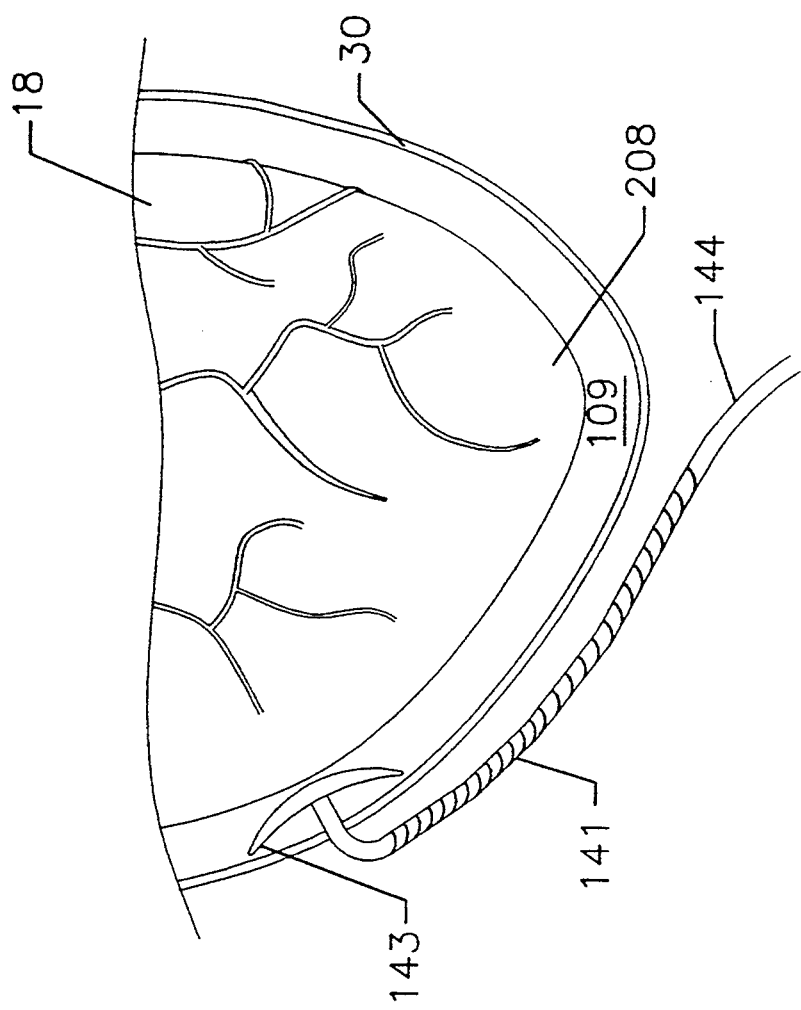
FIG. 24 shows an extrapericardial lead with an intrapericardial anchor.

A depiction of a lead anchor 143 is shown in FIGS. 24 and 25. The resilient flexible flange 143 is forced through a hold positioned at the appropriate spot in the pericardium. With traction applied to the lead, the concave flange seals and anchors against the pericardium. The lead anchor 143 can be used intrapericardially or extrapericardially.

Additional leads may be placed through additional sheaths placed by using the previously described procedure. Alternatively, additional sheaths or anchors may be guided or pulled into the pericardial space through access holes created from within the pericardial space. The guidewire tip may be manipulated under endoscopic guidance to a desired location. The needle may be advanced from the guidewire tip and an access hole may then be sliced or punctured through the pericardium. The needle would be retracted and the guidewire tip would be pulled out of the body through a percutaneous, mediastinal trocar. Next, a dilator and sheath (or lead anchor) would be advanced over the guidewire into the pericardium. Lead placement and anchoring for subsequent leads could be done as described above.

Figure 27:
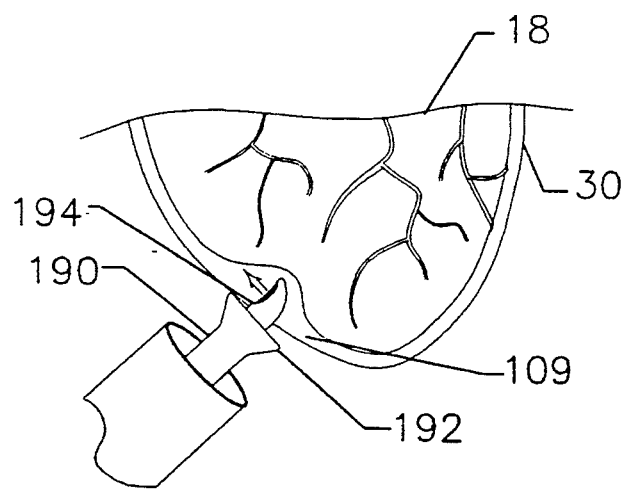
FIG. 27 shows a needle tip placed in the pericardial space surrounding a heart.

One way to penetrate the pericardium, as has been previously mentioned, is with a needle. A construction of a needle suited to cutting the pericardium is depicted in FIG. 27. This needle 190 includes a shoulder 192 to limit depth of penetration; the stick through the pericardium can thus be made more safely. Because the needle lumen exits to the side, a guidewire and/or infusate 194 can enter the pericardium space instead of impaling the myocardium. A further improvement on this construction employs a needle as described mounted on a flexible shaft, such as a braided polymeric tube. This allows the shaft to move with the heart contractions, and so reduces the hazard of inadvertent perforation.

In some applications, it may be desirable to insert a guidewire 198 immediately through the needle once pericardial access is gained. The wire 198 should include an anchor, such as a balloon 199 or the ability to deform the tip of the guidewire into an anchor loop. This would anchor as well as create space in the pericardium for subsequent introducer and lead placement. This may also be a good time to perform an infusion to create additional maneuvering space within the pericardium.

Figure 28:
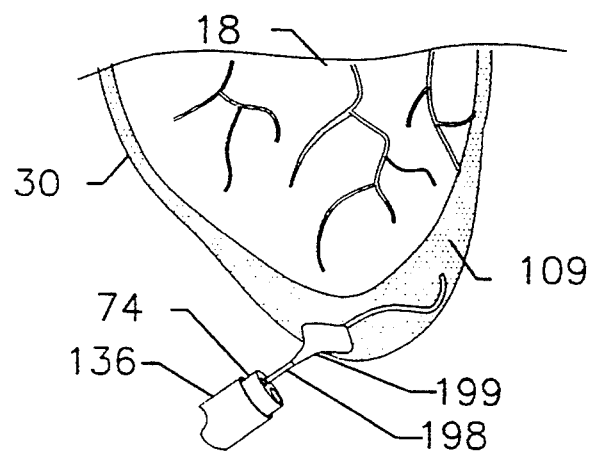
FIG. 28 shows a guidewire anchored within the pericardial space by an inflated balloon anchor.

Once placed, the needle should be removed promptly to avoid piercing coronary vessels or perforating the heart wall. In accordance with common clinical practice, a guidewire is placed through the needle and into the pericardium. FIG. 28 shows a guidewire already in place with the anchor 199 inflated. To avoid inadvertent punctures, and to avoid the unhappy circumstance of having the guidewire slip out, a special balloon tip guidewire 198 may be used. Once inflated, the balloon 199 can not easily slip out of the pericardium. The balloon 199 provides an anchor and the guidewire would serve as an anchorline. It should be noted that the balloon 199 could take many forms and may be made of any number of resilient materials such as latex, polyurethane, polyethylene, etc.

Epicardial access may also be obtained using a method that relies less on exacting skill than the preceding method does. This method resembles in part that of transdermal injections. A jet spray could deliver fluid across the pericardium without even creating any gross punctures that could potentially cause excessive arterial bleeding. Once a sufficient amount of fluid has been infused into the pericardial space, then a pericardial stick can easily, safely and conventionally be made.

Figure 29:
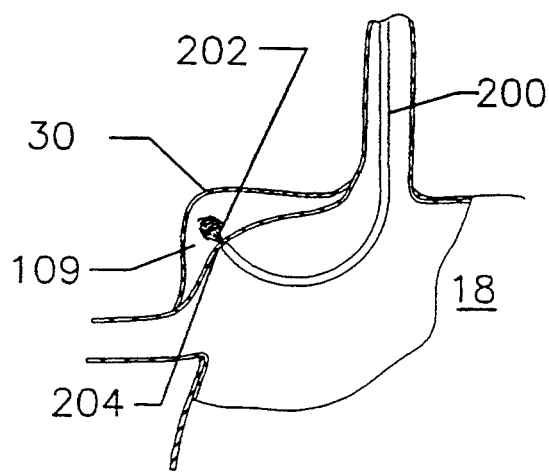
FIG. 29 shows a transvenous catheter placed in the heart.

An interesting, and potentially tremendously simplifying procedure employs a variation of the preceding construction method. The injection is made endocardially and transmyocardially. This should be much safer and more effective. A high pressure catheter 200 could be placed in the right atrium along the free wall as shown in FIG. 29. The tip position could be stabilized by a preformed tip, an actively deflected tip or any of a number of reversible, temporary catheter tip anchors. A fluid stream 202 directed out the catheter tip and accelerated by a nozzle 204 at the tip should readily create a pericardial effusion without even the need for any thoracic punctures. Consequently, an easy and safe target for a pericardial needle is created with virtually no risk of myocardial perforation or tamponade. The effusions should easily be contained by the pericardial sac due both to decrease in fluid pressure as it exits the catheter and contacts the tough pericardium.

Under certain circumstances, a surgeon may select not to use the pericardial space. This may be due to proliferative adhesions for example. Under such circumstances, the leads may still be readily deployed extrapericardially. Rather than deploying anchors through the pericardium, anchors may be deployed through the pleural sacs instead. In this way the electrodes will still be in very close proximity to the heart and also held relatively motionless with respect to the heart.

Figure 26:
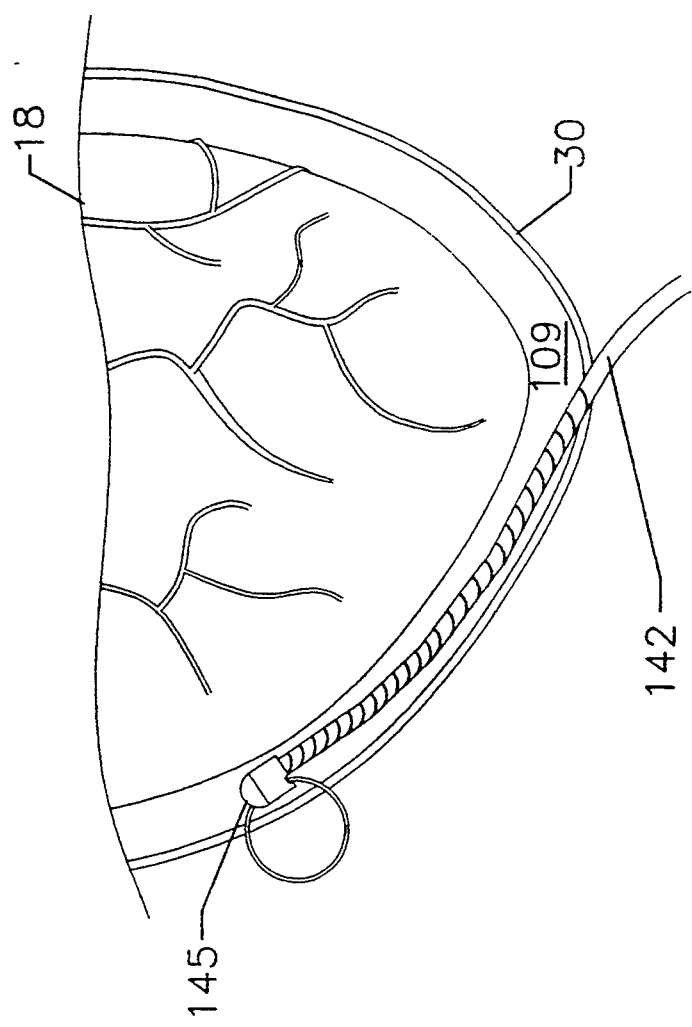
FIG. 26 show a formed wire anchored lead placed in the pericardial space.

Another lead anchor is depicted in FIG. 26. The lead tip is positioned in the pericardial space as described previously. Then a preformed wire is advanced from the proximal end through a lumen in the defibrillation lead. The wire pierces through the pericardium to the extra pericardial space. As the wire continues to advance it pierces the pericardium again and is sheathed and locked safety within the distal lead tip. The metal wire may have a round or flat (ribbon shape) cross-sectional area. In the preferred embodiment, the wire is a nitinol ribbon. Nitinol is selected for its ability to be deformed to a very small radius without breaking. A cross-sectional area having a ribbon shape is preferred over a round cross-sectional shape because it distributes the anchor force over a larger section of the pericardium.

While the present invention has been described in terms of preferred embodiments, it is to be understood that the invention is not to be limited to the exact form of the apparatus or processes disclosed. Therefore, it is to be understood that the invention may be practiced other than as specifically described without departing from the scope of the claims.

What is claimed is:

1. A system for implanting electrical leads in or on the pericardium of a heart, comprising:

a guiding catheter including distal end;

a suction cup having a bore therethrough and mounted to said distal end of said guiding catheter, said suction cup disposed to abut a pericardium surrounding said heart;

a vacuum pump coupled to said guiding catheter to evacuate said guiding catheter so that a pressure differential holds said suction cup to said pericardium when said suction cup abuts said pericardium;

an endoscope fitted through said guiding catheter for observing a surface of said pericardium through said bore of said suction cup;

a wire guide inserted through said guiding catheter, said wire guide having a distal end that includes first anchoring means for providing an anchoring function in the pericardium and a needle selectively deployable a predetermined distance from said distal end of said wire guide for cutting an access hole through a pericardium into said pericardial space;

a dilator having a blunt, tapered distal end and a longitudinal bore slidable over said wire guide so that said blunt end of said dilator may be advanced to penetrate and dilate said access hole;

a flexible sheath having a distal end fitted to slide over said dilator, said flexible sheath and said wire guide forming a channel when said dilator is withdrawn from said wire guide; and an electrical lead having a distal end equipped with second anchoring means for anchoring the distal end of the electrical lead to body tissue, said electrical lead and distal end being of a size and shape that permits the insertion of the electrical lead through the channel of said flexible sheath so that the distal end of said electrical lead passes through said access hole into said pericardial, space, said distal end being adapted to be anchored in said pericardial space by said second anchoring means.

2. The system of claim 1 wherein said suction cup is bell-shaped and manufactured of a resilient material.

3. The system of claim 1 wherein said wire guide comprises:

a flexible wire tube formed of helically coiled wire and having a distal end, said tube having an inside surface defining a bore therethrough;

a blunt end cap attached to said distal end of said flexible wire tube and having an aperture therethrough;

a weld bead welded longitudinally along the inside surface of said wire tube;

an actuation wire welded along the inside surface of said flexible wire tube and extending longitudinally along the length of said tube, said actuation wire positioned diametrically opposite of said weld bead, whereby the distal end of said flexible wire tube may be selectively deflected into said "J"-shape by applying tension to said actuation wire;

a needle guide tube positioned within said flexible wire tube and extending the length of said flexible wire tube; and a hollow needle positioned to slide within said needle guide tube, said hollow needle selectively deployable through said aperture of said end cap.

4. The system of claim 3 wherein said helically coiled wire is manufactured of stainless steel.

5. The system of claim 1 wherein said electrical lead includes:

helically wound electrically conductive wire having proximal and distal ends;

an insulating sheath formed over said helically wound electrically conductive wire such that the distal end of said helically wound electrically conductive wire is exposed; and an end cap having a bore therethrough mounted to the distal end of said helically wound wire, said end cap having barbs extending therefrom which permit penetration of the distal end of said helically coiled electrically conductive lead wire into said pericardial space to secure said distal end of said helically coiled electrically conductive lead wire in said pericardial space.

6. The system of claim 1 further including a trocar having a bore therethrough through which the guiding catheter is inserted.

* * * * *